United States Patent [19]

Jackson et al.

[11] Patent Number: 5,849,774

[45] Date of Patent: *Dec. 15, 1998

[54] TREATMENT OF SEPSIS-INDUCED ACUTE RENAL FAILURE

[75] Inventors: Edwin K. Jackson; Joseph A. Carcillo, both of Pittsburgh, Pa.

[73] Assignee: University of Pittsburgh, Pittsburgh, Pa.

[*] Notice: This patent issued on a continued prosecution application filed under 37 CFR 1.53(d), and is subject to the twenty year patent term provisions of 35 U.S.C. 154(a)(2).

[21] Appl. No.: 675,115

[22] Filed: Jul. 3, 1996

[51] Int. Cl.$^6$ .................................................. A61K 31/415
[52] U.S. Cl. ................................................ 514/392
[58] Field of Search ............................................... 514/392

[56] References Cited

PUBLICATIONS

Beavo, J.A., et al., *Mol. Pharmacol.* 46:399 (1994):.
Beavo, J.A., et al., *TIPS* 11:150 (1990).
Morrison, D.C.,, et al., *Annu. Rev. Med.* 38:416 (1987).
Turney, J.H., et al., *Q.J. Med.* 74:83 (1990).
Brackeen, M.F., et al., *J. Med. Chem.* 38:4848 (1995).
Stafford, J.E., et al., *J. Med. Chem.* 38:4972 (1995).
Heaslip, R.J., et al., *J. Pharmacol. Exp. Ther.* 268:888 (1994).
Ashton, M.J., et al., *J. Med. Chem.* 37:1696 (1994).
Verghese, M.W., et al., *J. Pharmacol. Exp. Ther.* 272:1313 (1995).
Feldman, P.L., et al., *J. Med. Chem.* 38:1505 (1995).
Landow, L., et al., *Acta Anaesths. Scand.* 38(7):626 (1994).
Liu, P., et al., *Shock* 3(1):56 (1995).
Kambayashi, T., et al., *J. Immun.* 155:4909 (1995).
Sekut, L., et al., *Clin. Exp. Immunol.* 100(1):126 (1995).
Dent, G., et al., *J. Pharmacol. Exp. Ther.* 271:1167 (1997).
Chini, C., et al., *Kidney Int.* 46:28 (1994).
Fisher, W., et al., *Biochem. Pharmacol.* 45:2399 (1993).
Cardelus, I., et al., *E.J. Pharmacol.* 299:153 (1996).
HCAPLUS abstract, AN 1996:435288, Begany et al. (1996).
HCAPLUS abstract, AN 1973:67018, Hamilton (1972).
HCAPLUS abstract, AN 1994:236189, Stief et al., (DE 4230755), 1994.

*Primary Examiner*—Zohreh Fay
*Assistant Examiner*—M. Moezie
*Attorney, Agent, or Firm*—Reed Smith Shaw & McClay LLP

[57] ABSTRACT

Methods are provided for treating sepsis/endotoxin-induced acute renal failure, and renal vasoconstriction and catecholamine-induced renal and mesenteric vasoconstriction by administering to a patient a therapeutically effective amount of a composition comprising at least one drug with Type IV phosphodiesterase inhibiting activity or any combination thereof and a pharmaceutically acceptable carrier.

4 Claims, 18 Drawing Sheets

TREATMENT OF SEPSIS-INDUCED ACUTE RENAL FAILURE

FIELD OF THE INVENTION

The present invention relates generally to the treatment of mammalian endotoxemia and septicemia and renal and mesenteric vasoconstriction that is induced by catecholamines that are used to treat endotoxemia and septic shock. More particularly, the present invention relates to the inhibition of Type IV phosphodiesterases to treat such conditions.

BACKGROUND OF THE INVENTION

Phosphodiesterases ("PDEs") are a class of enzymes that inactivate/metabolize cyclic AMP and cyclic GMP, two naturally occurring substances that cause a number of physiological effects. There are at least seven different families/types of phosphodiesterase gene families, with several gene families containing multiple genes and/or splice variants as reported by Beavo, J. A., et al., *Mol. Pharmacol.* 6:399 (1994) and Beavo, J. A., et al., *TIPS* 11:150 (1990), the disclosures of which are incorporated herein by reference.

Most tissues in the body contain one or more PDE enzymes, so that drugs that inhibit all families of PDE elicit too many side effects to be of clinical value. The recent development of class-specific PDE inhibitors provides the opportunity to develop new therapeutic strategies that rely on tissue-specific differences in the distribution of specific types of PDEs to target therapeutic outcomes with minimal patient side effects.

Sepsis caused by Gram-negative bacteria is often accompanied by acute renal failure, that is, a rapid decline in renal function characterized by an increase in renal vascular resistance, a reduction in renal blood flow and a decrease in glomerular filtration rate. The cell walls of Gram-negative bacteria release the toxic lipopolysaccharide endotoxin during systemic infection and several of the effects of Gram-negative sepsis are initiated by the release of endotoxin into the system circulation, including acute renal failure in humans and animals. See, Morrison, D.C., et al., *Annu. Rev. Med.* 38:416 (1987), the disclosure of which is incorporated herein by reference. Sepsis-induced acute renal failure is a serious medical condition because it frequently leads to multiple organ failure and a greater than 60% mortality rate as reported by Turney, J. H., et al., *O.J. Med.* 74:83 (1990), the disclosure of which is incorporated herein by reference. Currently the treatment options for this condition are limited and bad outcomes frequently occur.

The catecholamine norepinephrine is a potent vasopressor that is used as a therapy during septic shock and endotoxemia. Norepinephrine stimulates the $\beta_1$-adrenergic receptor which increases heart contractility, and the $\alpha$-adrenergic receptors which increase vasoconstriction. The combined effects of norepinephrine result in an increase in blood pressure during shock states. Unfortunately, norepinephrine also potently induces vasoconstriction in the renal and mesenteric vascular beds which severely limits its clinical efficacy.

In light of the foregoing, a need remains for methods to attenuate endotoxin-induced renal vasoconstriction and endotoxin-induced acute renal failure without inducing serious systemic side effects. Additionally, once a subject is afflicted with endotoxemia and has been treated with a vasopressor such as norepinephrine there is a need to attenuate renal and mesenteric ischemia. Clearly, a need also remains for methods to prevent mortality of subjects inflicted with endotoxemia that have either received or not received vasopressor agents.

SUMMARY OF THE INVENTION

Accordingly, it is a primary object of the present invention to provide a method for treating septicemia/endotoxemia.

Another object of the present invention is to provide a method for treating acute renal failure caused by septicemia/endotoxemia.

Yet another object of the present invention is to provide a method for treating renal vasoconstriction caused by septicemia/endotoxemia.

Yet another object of the present invention is to provide a method for attenuating catecholamine-induced renal and mesenteric vasoconstriction.

Still yet another object of the present invention is to provide a method to prevent damage to a patient's intestines and kidney due to the effects of endotoxin and/or vasopressor agents.

These and other objects of the present invention are achieved by one or more of the following embodiments.

In one aspect, the invention features a method for attenuating sepsis/endotoxin-induced acute renal failure in a subject at risk of septicemia/endotoxemia comprising the step of administering to the subject prior to the onset of septicemia/endotoxemia a therapeutically effective amount of a composition comprising at least one drug with Type IV phosphodiesterase inhibiting activity or any combination thereof and a pharmaceutically acceptable carrier.

In another aspect, the invention features a method for attenuating sepsis/endotoxin-induced acute renal failure in a subject comprising the step of administering to the subject after the onset of septicemia/endotoxemia a therapeutically effective amount of a composition comprising at least one drug with Type IV phosphodiesterase inhibiting activity or any combination thereof and a pharmaceutically acceptable carrier.

In yet another aspect, the invention features a method for attenuating or preventing catecholamine-induced renal and mesenteric ischemia in a subject comprising the step of administering to the subject after the onset of septicemia/endotoxemia a therapeutically effective amount of a composition comprising at least one drug with Type IV phosphodiesterase inhibiting activity or any combination thereof and a pharmaceutically acceptable carrier.

In preferred embodiments, the Type IV phosphodiesterase inhibitor is Ro 20-1724.

Other features and advantages of the invention will be apparent from the following description of the preferred embodiment, and from the claims.

DETAILED DESCRIPTION OF THE INVENTION

I. DEFINITIONS

Figure 1:
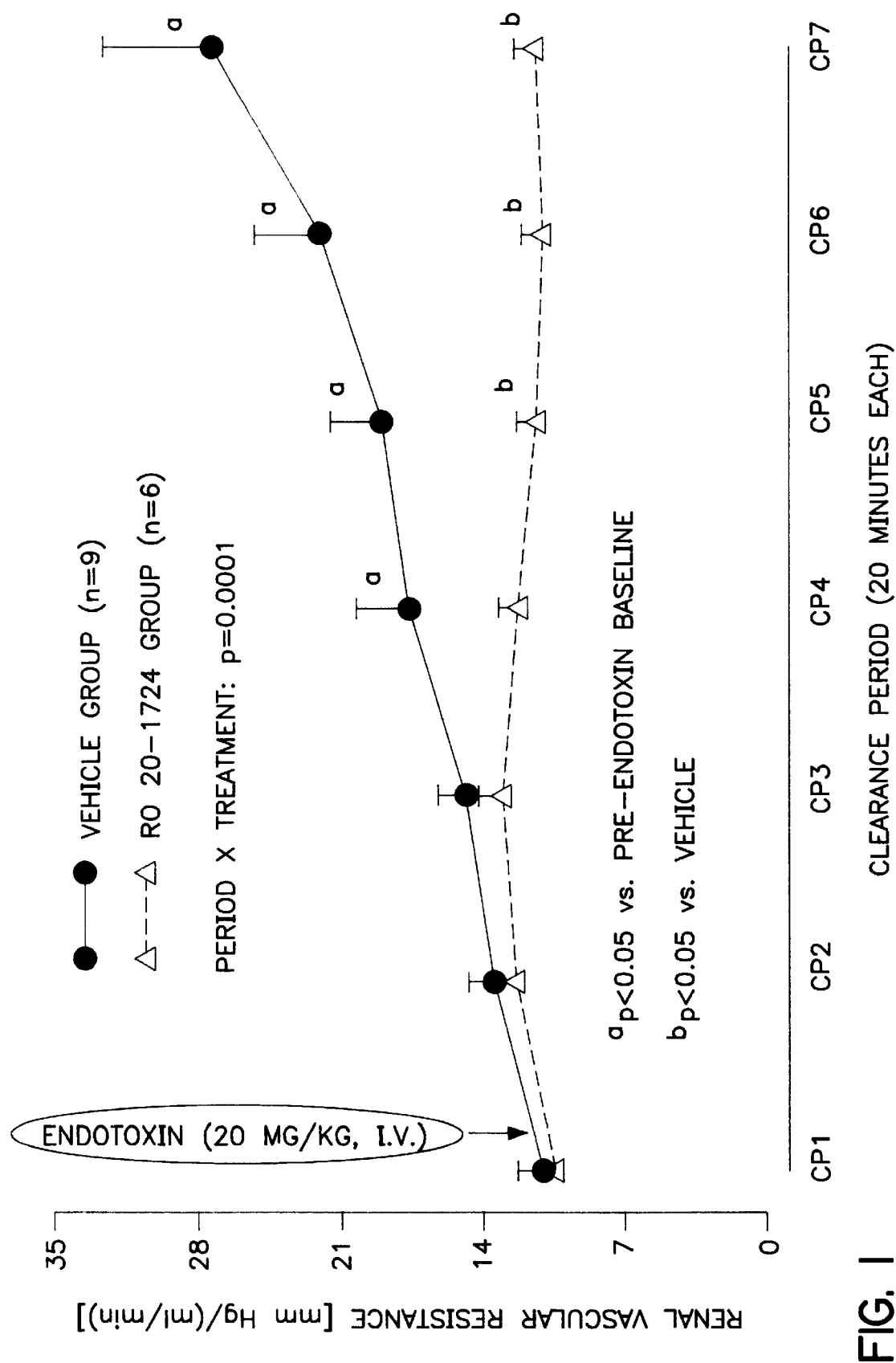
FIG. 1 shows the effects of endotoxin on renal vascular resistance in rats pre-treated with either vehicle (●) or Ro 20-1724 (Δ). Values are mean ±S.E.

As used herein, the term "acute renal failure" means a rapid deterioration in renal function sufficient to result in accumulation of waste products in the body. "Arterial blood pressure" refers to the hydrostatic pressure of the blood in the arteries. "Catecholamine" refers to any compound that contains a catechol and an amine and has a sympathomimetic action. Examples include, but are not limited to, norepinephrine, epinephrine, dopamine and dobutamine.

The term "endotoxemia" refers to the presence of microbial endotoxins in the bloodstream. Subjects inflicted with endotoxemia usually also have septicemia. Therefore the terms septicemia and endotoxemia are used interchangeably and are also referred to herein as "septicemia/endotoxemia".

An "endotoxin" refers to any harmful components of microbial cells such as lipopolysaccharides from the Gram-negative bacterial cell wall, peptidoglycans from Gram-positive bacteria, and mannan from fungal cell walls. "Glomerular filtration rate" means the volume per unit time of blood plasma that is filtered by the kidneys.

As used herein, "ischemia" refers to a reduction in blood flow to an organ. "Mean arterial blood pressure" is the average (arithmetic mean) arterial blood pressure over a defined period of time. "Mesenteric vascular resistance" refers to the hindrance to blood flow through the mesenteric artery which supplies blood to the intestines. Mesenteric vascular resistance is calculated by dividing arterial blood pressure by mesenteric blood flow. "Mesenteric blood flow" refers to the volume of blood per unit time passing through the mesenteric artery.

The term "phosphodiesterase" refers to any enzyme that hydrolyzes one of two ester linkages on a single phosphate group.

"Renal vascular resistance" refers to the hindrance to blood flow through the renal artery which supplies blood to the kidneys. Renal vascular resistance is calculated by dividing mean arterial blood pressure by renal blood flow.

"Renal blood flow" means the volume of blood per unit time passing through the mesenteric artery.

The terms "sepsis" and "septicemia" refer to a morbid condition resulting from the invasion of the bloodstream by microorganisms and their associated endotoxins. A subject with septicemia also has endotoxemia and therefore the terms septicemia and endotoxemia are used interchangeably and are also referred to herein as "septicemia/endotoxemia".

As used herein, "Type IV phosphodiesterase" refers to any cyclic nucleotide phosphodiesterase that selectively metabolizes cyclic-3',5'-adenosine monophosphate ("cyclic AMP" or "cAMP"), and has a low affinity for cyclic-3',5'-guanosine monophosphate ("cyclic GMP" or "cGMP"). Unlike most other families of cyclic nucleotide phosphodiesterases, the enzymatic activity of the Type IV phosphodiesterases is not significantly modulated by cyclic GMP or calcium/calmodulin. Moreover, Type IV phosphodiesterases are potently inhibited by agents such as Ro 20-1724 and rolipram. Although initially defined by biochemical and pharmacological criteria, the genes encoding Type IV phosphodiesterases have been cloned and the protein structures of Type IV phosphodiesterases have been elucidated (see, Beavo, J. A., et al., *Mol. Pharmacol.* 6:399 (1994), the disclosure of which is incorporated herein by reference).

"Vasoconstriction" refers to a reduction in the diameter of blood vessels due to contraction of the muscular walls of the blood vessel. Vasoconstriction leads to ischemia.

II. METHODS AND RESULTS

According to the present invention methods are provided to treat septicemia/endotoxemia in humans and other mammals. The terms "patients" and "subjects" as used herein include both humans and other mammalian animals. Septicemia/endotoxemia leads to renal vasoconstriction and acute renal failure. Moreover, catecholomines such as norepinephrine which are frequently used to support blood pressure in patients afflicted with septicemia actually worsen renal vasoconstriction and cause splanchnic vasoconstriction. The present invention provides methods for attenuating renal vasoconstriction and acute renal failure caused by septicemia/endotoxemia infection. Also provided are methods for attenuating renal and mesenteric vasoconstriction that is induced by catecholamine treatment of septicemia and endotoxemia.

It has been found that pretreatment of patients with Type IV phosphodiesterase inhibitors, that is before the subject is exposed to endotoxin, substantially prevents endotoxin-induced renal vasoconstriction and attenuates endotoxin-induced renal failure. It has also been found that treating patients with Type IV PDE inhibitors after exposure to endotoxin can attenuate endotoxin-induced acute renal failure and can further prevent norepinephrine-induced renal and mesenteric ischemia without a decrease in systemic blood pressure. Additionally, it has been found according to the present invention that treatment with a Type IV PDE inhibitor such as Ro 20-1724 can lessen mortality in the presence or absence of vasopressor infusions.

The active ingredient used in the method of the present invention is any compound or drug with Type IV PDE inhibiting activity or combination thereof. In the preferred embodiment, the Type IV PDE inhibitor is Ro 20-1724 with the formula 4-[(3-butoxy-4-methoxyphenyl) methyl]-2-imidazolidinone as described by Brackeen, et al., *J. Med. Chem.* 38:4848 (1995), the disclosure of which is incorporated herein by reference. Other examples of Type IV PDE inhibitors which may also be used to carry out the methods of the present invention include GW3600 as described by Statford, et al., *J. Med. Chem.* 38:4972 (1995); WAY-PDA-641 as described by Heaslip, et al., *J. Pharmacol. Exp. Ther.* 268:888 (1994); RP 73401 as described by Ashton, et al., *J. Med. Chem.* 37:1696 (1994); CP-77059 as described by Verghese, et al., *J. Pharmacol. Exp. Ther.* 272:1313 (1995); 7-[3-(cyclopentyloxy)-4-methoxyphenyl] hexahydropyrrolo [1,2-c] imidazol-3-one; 7-[3-(cyclopentyloxy)-4-methoxyphenyl] tetrahydropyrrolo [1,2-c] oxazol-3-one; 7-[3-(cyclopentyloxy)-4-methoxyphenyl] hexahydropyrrolizidin-3-one, as described by Brackeen, et al., *J. Med. Chem.* 38:4848 (1995); 1-acetyl-3-(3-cyclopentoxy-4-methoxyphenyl) pyrrolidine, and 1-ureido-3-(3-cyclopentoxy-4-methoxyphenyl) pyrrolidine as described by Feldman, et al.,*J. Med. Chem.* 38:1505 (1995); and rolipram as described by Brackeen, et al., *J. Med. Chem.* 38:4848 (1995), all the disclosures of which are incorporated herein by reference.

The present Type IV PDE inhibiting compounds may preferably be effectively used for the treatment of sepsis-induced acute renal failure, sepsis-induced renal vasoconstriction, cathecholamine-induced renal vasoconstriction, catecholamine-induced mesenteric vasoconstriction, and mesenteric and/or renal ischemia. Patients for which the subject therapy is indicated include children and adults with sepsis, acute renal failure, mesenteric and/or renal ischemia or multiple organ failure.

The pharmaceutical composition used in the methods of the present invention comprises at least one Type IV PDE inhibitor, such as, for example, Ro 20-1724, and a pharmaceutically acceptable additive or carrier. By selecting the additives, the composition may be formulated for the various administration routes as those of ordinary medicines, for example, intravenously, intramuscularly, subcutaneously, intraperitoneally, transdermally, orally, rectally, or intramucosally in an amount effective to inhibit Type IV PDE. In particular, the preferred dosage for use in the present invention elevates cAMP levels in body fluids such as urine and plasma.

For oral administration, the pharmaceutical composition may be formulated as, for example, pills, tablets, capsules, granules, dispersions, powders, suspensions, liquids, syrups, spirits, and the like. The injections are, for example, solutions, suspensions, or emulsions. The intramucosal formulation is, for example, suppositories. The transdermal formulations are, for example, patches, creams, ointments, gels, or lotions. Depending upon the manner of administration, the compounds may be formulated in a variety of ways. Pharmaceutically acceptable carriers include any physiological saline, such as normal saline, excipients, sugars, alum, dimethylsulfoxide ("DMSO"), and the like.

The route of administration of the subject compositions to carry out the methods of the present invention is preferably intravenously, but other routes of administration of suitably formulated compounds may also be utilized.

The preferred dose of Type IV PDE inhibitor varies according to the route of administration, the pharmacokinetic characteristics of the Type IV PDE inhibitor, and the condition of the mammalian subject, but is sufficient to elevate cAMP levels in the subject's body fluids such as urine and plasma. The preferred percentage increase in urinary excretion is on the order of about 100%, but will vary with the severity of the condition to be treated, and the route of administration and may be higher or lower depending on the dose. The dose frequently will also vary according to the age, body weight, and response of the individual patient. It is noted that the physician or clinician will know how and when to adjust, interrupt, or terminate therapy in conjunction with individual patient response. The term "therapeutically effective amount" or like term is encompassed by the above-described dosage guidelines.

The methods of the present invention, as will be illustrated by the examples that follow, may be advantageously practiced both prior to the onset of septicemia, in, for example, gun shot victims, knifing victims, car accident victims, and military personnel as well as other patients that are at high risk for septicemia, as well as after the onset of septicemia.

The present invention will now be further illustrated by, but is by no means limited to, the following examples. It will be apparent to those skilled in the art that many modifications, both to materials and methods, may be practiced without departing from the purpose and interest of this invention.

In the following example, the Type IV-specific phosphodiesterase inhibitor Ro 20-1724 was used to confer protection during endotoxin-induced renal failure in mammalian subjects.

EXAMPLE 1

Methods

Male Sprague-Dawley rats (399±6 g; mean±S.E.; n=23) were obtained from Charles River (Wilmington, Mass.) and were housed for at least 1 week in an animal care facility prior to administration of any treatments. Institutional guidelines for animal welfare were followed. The rats were fed Wayne Rodent Blox 8604 (Harlan TekLad, Madison, Wis.) containing 135 mEq/kg sodium and 254 mEq/kg potassium. The rats also were given water ad libitum. The rats were then anesthetized with Inactin (Research Biochemicals Intl., Natick, Mass.) (thiobutabarbital sodium 100 mg/kg intraperitoneally) and placed on a Deltaphase Isothermal Pad (Braintree Scientific, Braintree, Mass.). The body temperatures of the rats were monitored with a digital rectal probe thermometer (Physiotemp Instruments, Clifton, N.J.). The body temperatures of the rats were maintained at 37° C. by adjusting a heat lamp above the animals.

The trachea of each rat was cannulated with a PE-240 catheter (Clay Adams, Parsippany, N.J.) to facilitate respiration. A PE-50 catheter and a PE-10 catheter were inserted into the left jugular vein of each rat, and an infusion of 0.9% saline was begun at 100 µl/min in the PE-50 catheter using a Model BSP 99 Braintree infusion pump. A PE-50 catheter was placed in the left carotid artery and attached to a Micro-Med digital blood pressure analyzer (Micro-Med, Inc., Louisville, Ky.) for continuous monitoring of mean arterial blood pressure and heart rate. The abdominal cavity was then exposed through a midline incision, and a transit-time blood flow probe was placed around the left renal artery (Model 1 RB, Transonic Systems, Inc., Ithaca, N.Y.). The blood flow probe was connected to a small-animal digital, transit-time blood flowmeter (Model T206, Transonic Systems, Inc.), and renal blood flow was continuously displayed. The left ureter was cannulated with PE-10 tubing for urine collection.

After completion of the surgical procedure, the jugular saline infusion described above was replaced with an infusion of [$^{14}$C]carboxyl-inulin marker in 0.9% saline (DuPont-NEN, Boston, Mass.) (0.5 µCi bolus, followed by 0.035 µCi/min at 100 µl/min). The rats were then randomized and an infusion of Ro 20-1724 (10 µg/kg/min, n=10) (Research Biochemicals, Intl.) or vehicle (4 µl/min dimethylsulfoxide ("DMSO") (Sigma Chemical, St. Louis, Mo.), n=13) via the jugular PE-10 catheter was begun. After a 1 hour stabilization period, a 20 minute urinary clearance period (also referred to below as "period 1" or "CP1"), with a midpoint blood sampling, was performed. Mean arterial blood pressure and heart rate ("HR") were time-averaged over the 20 minute clearance period, and renal blood flow ("RBF") was recorded at 10 and 20 minutes into the clearance period.

Six of the Ro-1724-treated rats and nine of the vehicle-treated rats then received 20 mg/kg endotoxin (*Escherichia coli* LPS, serotype 026:B6; Sigma Chemical Co., St. Louis, Mo.) intravenously over 10 minutes, followed by a 30 minute rest period. Four Ro 20-1724-treated rats and four vehicle-treated rats received only the vehicle (saline) for endotoxin to establish the effects of Ro 20-1724 in the absence of endotoxin and to evaluate the stability of the experimental model in the absence of endotoxin. Then, six successive 20 minute urinary clearance periods (referred to below as "period x"/"CPx") were conducted with mid-point blood sampling and recording of mean arterial blood pressure, heart rate, and renal blood flow performed as described above for clearance period 1. Urine volumes for all periods were measured and recorded.

Renal blood flow was taken as the average of the two measurements recorded for each clearance period, and renal vascular resistance ("RVR") was calculated as MABP/RBF. Glomerular filtration rate ("GFR") was determined as the renal clearance of [$^{14}$C]carboxyl-inulin, which was quantified with the use of liquid scintillation analysis of serum and urine samples using a Tri-Carb Model 2500TR (Packard Instrument Co., Meriden, Conn.).

Urine samples were analyzed for cAMP concentration as follows. Briefly, urine was centrifuged at 14,000 rpm in a microcentrifuge for 2 minutes, and ~0.2 ml of urine was mixed with 20 µl of 10 µM 9-D-arabinofuranosyladenine (internal standard) and 1 ml of 0.5M ammonium sulfate, pH 9.3. The samples were applied to a $C_{18}$ Sep-Pak cartridge (Waters, Corp., Milford, Mass.) that had been preconditioned with 3 ml of methanol followed by 3 ml of deionized water. The Sep-Pak was washed with 5 ml of 5 mM ammonium sulfate, pH 9.3, and cAMP was eluted with 2 ml of 10% methanol in 10 mM phosphoric acid. The last 1.5 ml of eluant was collected. Then, 40 µl of 0.5M acetate buffer, pH 4.8, and 40 µl of 50% chloroacetaldehyde in water were added to the 1.5 ml of eluant, and the samples were heated for 1 hr at 80° C. 80 µl of each sample were then injected into an Isco, Inc. (Lincoln, Neb.) high-pressure liquid chromatograph (pump model 2350, gradient programmer model 2360, 4.6×250 mm $C_{18}$ column). Wavelengths for excitation and emission were set at 275 and 420 nm, respectively, and were monitored with a Waters model 470 scanning fluorescent detector. The mobile phase was 95.5% citrate-phosphate buffer (0.014M citric acid and 0.017M $Na_2HPO_4$) and 4.5% acetonitrile with a flow rate of 1.2 ml/min. The peak areas for cAMP and internal standard were calculated, and the concentration of cAMP was quanitified through a comparison of the ratio of peak areas with a standard curve.

Statistical significance was evaluated using repeated measures analysis of variance (one- and two-factor) and Student's t-tests and was performed using the Number Cruncher Statistical System (Kaysville, Utah).

Results

Table 1 shows some the various parameters in control and Ro 20-1724-treated rats that did not receive endotoxin:

TABLE 1

Parameters in Time Control Rats
(Animals Not Receiving Endotoxin)

| | Period 1 | Period 2 | Period 3 | Period 4 | Period 5 | Period 6 | Period 7 |
|---|---|---|---|---|---|---|---|
| | | | mmHg | | | | |
| MABP | | | | | | | |
| Control | 133 ± 2 | 144 ± 3 | 144 ± 3 | 145 ± 4 | 146 ± 3 | 145 ± 4 | 144 ± 4 |
| Ro 20-1724 | 132 ± 1 | 133 ± 2 | 136 ± 2 | 139 ± 3 | 139 ± 3 | 137 ± 3 | 136 ± 3 |

TABLE 1-continued

Parameters in Time Control Rats
(Animals Not Receiving Endotoxin)

| | Period 1 | Period 2 | Period 3 | Period 4 | Period 5 | Period 6 | Period 7 |
|---|---|---|---|---|---|---|---|
| | | | beats/min | | | | |
| HR | | | | | | | |
| Control | 352 ± 4 | 357 ± 7 | 354 ± 7 | 354 ± 8 | 362 ± 8 | 368 ± 9 | 379 ± 13 |
| Ro 20-1724 | 357 ± 11 | 362 ± 11 | 364 ± 11 | 368 ± 10 | 368 ± 9 | 371 ± 9 | 368 ± 10 |
| | | | $\mu$V20 min | | | | |
| Urine volume | | | | | | | |
| Control | 920 ± 145 | 1573 ± 158[a] | 1790 ± 147[a] | 1938 ± 133[a] | 2268 ± 257[a] | 2002 ± 146[a] | 2430 ± 401[a] |
| Ro 20-1724 | 642 ± 78 | 1091 ± 106[a] | 1373 ± 101[a] | 1620 ± 100[a] | 1624 ± 105[a] | 1586 ± 150[a] | 1593 ± 157[a] |
| | | | mm Hg/(mVmin) | | | | |
| RVR | | | | | | | |
| Control | 11.3 ± 0.43 | 11.7 ± 0.46 | 11.5 ± 0.43 | 11.3 ± 0.40 | 11.3 ± 0.40 | 11.5 ± 0.31 | 11.7 ± 0.26 |
| Ro 20-1724 | 11.2 ± 0.62 | 10.7 ± 0.81 | 10.8 ± 0.71 | 11.1 ± 0.66 | 11.9 ± 0.67 | 12.2 ± 0.92 | 12.6 ± 1.12 |
| | | | mVmin | | | | |
| RBF | | | | | | | |
| Control | 12.0 ± 0.34 | 12.4 ± 0.30 | 12.6 ± 0.37 | 13.0 ± 0.42 | 13.1 ± 0.41 | 12.6 ± 0.35 | 12.4 ± 0.35 |
| Ro 20-1724 | 12.2 ± 0.56 | 13.1 ± 0.72 | 13.1 ± 0.63 | 12.9 ± 0.57 | 12.1 ± 0.51 | 11.9 ± 0.70 | 11.7 ± 0.77 |
| GFR | | | | | | | |
| Control | 1.62 ± 0.05 | 1.69 ± 0.06 | 1.70 ± 0.04 | 1.76 ± 0.02 | 1.91 ± 0.07 | 1.76 ± 0.04 | 1.85 ± 0.11 |
| Ro 20-1724 | 1.69 ± 0.04 | 1.75 ± 0.04 | 1.77 ± 0.03 | 1.80 ± 0.03 | 1.73 ± 0.03 | 1.75 ± 0.07 | 1.70 ± 0.02 |
| Urinary cAMP excretion | | | | | | | |
| Control | 2.0 ± 0.14 | 1.9 ± 0.08 | 1.7 ± 0.06 | 1.6 ± 0.10 | 1.8 ± 0.09 | 1.7 ± 0.08 | 2.0 ± 0.15 |
| Ro 20-1724 | 3.6 ± 0.09[b] | 3.4 ± 0.20[b] | 3.4 ± 0.22[b] | 3.7 ± 0.27[b] | 3.4 ± 0.21[b] | 3.4 ± 0.12[b] | 3.6 ± 0.09[b] |

Values are mean ± S.E. for 4 rats
[a]$P < .05$ vs. period 1
[b]$P < .05$ vs. control Table 1 above shows all the measured parameters in the time control rats, i.e., rats that received either vehicle or Ro 20-1724 but which did not receive endotoxin. The results show that mean arterial blood pressure "MABP", heart rate "HR", renal vascular resistance "RVR", renal blood flow "RBF", and glomerular filtration rate "GFR" were similar in vehicle-treated versus Ro 20-1724-treated rats. These parameters were stable over the duration of the experiment in both groups. Urinary cAMP excretions were significantly elevated in the Ro-1724-treated rats as compared with the vehicle-treated rats at all experimental periods. Within both groups, the cAMP excretion rates were stable over the course of the experiment. Urine volumes were similar in both groups, and in both groups, urine volumes gradually increased throughout the duration of the experiment.

In rats that were treated with endotoxin, urinary cAMP excretion rates were measured only during clearance periods 1, 4 and 7 since the time control studies indicated uniform effects of Ro 20-1724 over all seven periods. Urinary cAMP excretion rates were increased ($P<0.001$; $P=0.002$; and $P<0.001$, respectively) in animals treated with Ro 20-1724 (4.83±0.42; 6.17±0.89; and 5.52±0.57 nmol per 20 minutes for periods 1, 4, and 7, respectively) as compared with vehicle-treated animals (2.79±0.28; 2.67±0.44; and 1.78±0.42 nmol per 20 minutes for periods 1, 4, and 7, respectively). It is to be noted that in the Ro 20-1724-treated rats, cAMP excretion did not decrease after administration of endotoxin, whereas in the vehicle-treated rats that received endotoxin, the cAMP excretion rate declined significantly ($P<0.05$) during the seventh period.

Figure 2:
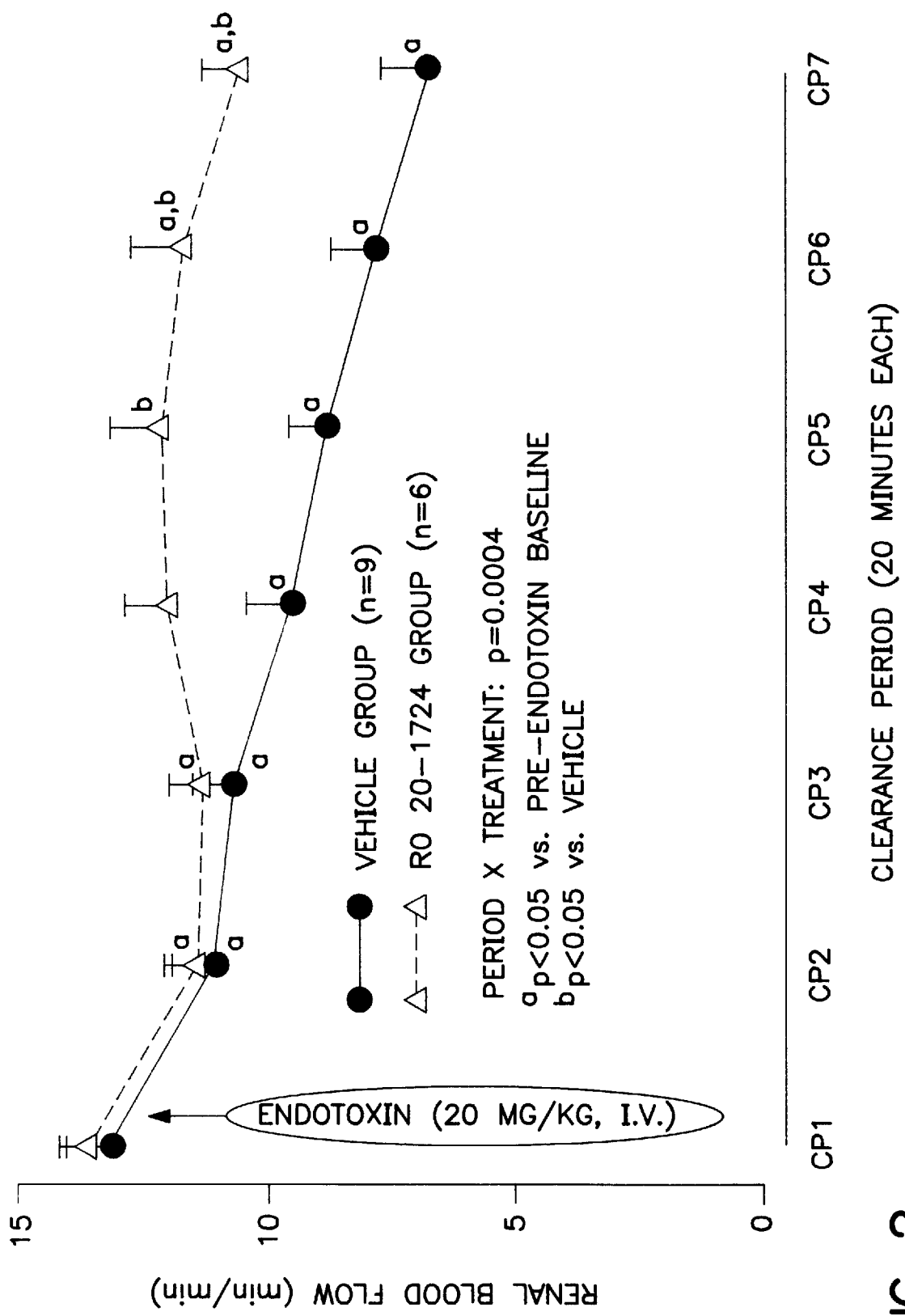
FIG. 2 shows the effects of endotoxin on renal blood flow in rats pre-treated with either vehicle (●) or Ro 20-1724 (Δ). Values are mean ±S.E.

As seen in FIG. 1, Ro 20-1724 conferred virtually complete protection ($P=0.0001$) against endotoxin-mediated increases in renal vascular resistance as compared to control animals which received only vehicle and endotoxin. Additionally, as shown in FIG. 2, Ro 20-1724 significantly attenuated endotoxin-induced reductions in renal blood flow as compared to the control animals.

Figure 3:
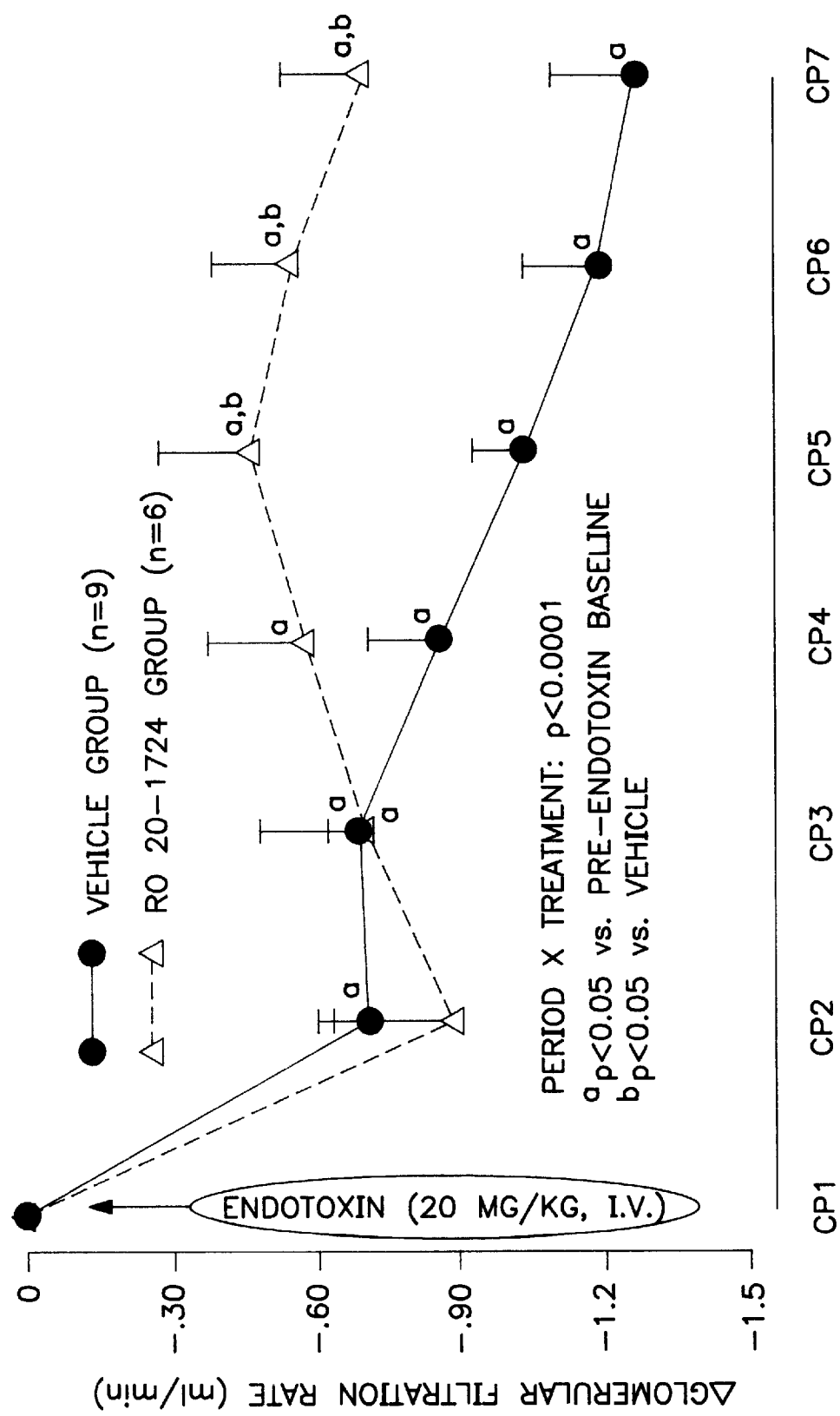
FIG. 3 shows the effects of endotoxin on glomerular filtration rate in rats pre-treated with either vehicle (●) or Ro 20-1724 (Δ). Base-line (CP1) values for glomerular filtration rates were 2.29±0.03 and 2.04±0.19 for the vehicle-treated and Ro 20-1724-treated rats, respectively. Values are mean ±S.E.

FIG. 3 shows that during the first clearance period after the administration of endotoxin, glomerular filtration rate declined to a similar extent in the vehicle-treated and Ro 20-1724-treated rats. However, although glomerular filtration rate continued to decline in subsequent clearance periods in vehicle-treated animals, glomerular filtration rate recovered to near normal levels in the Ro 20-1724-treated rats ($P=0.0001$).

Table 2 below shows the mean arterial blood pressure, heart rate, and urine volume in control and Ro 20-1724-treated animals that received endotoxin.

TABLE 2

Mean Arterial Blood Pressure (MABP), Heart Rate (HR) and Urine Volume In Control (n = 9) and Ro 20-1724-Treated Rats (n = 6)

|  | Period 1 | Period 2 | Period 3 | Period 4 | Period 5 | Period 6 | Period 7 |
|---|---|---|---|---|---|---|---|
| | | | | mmHg | | | |
| MABP | | | | | | | |
| Control | 135 ± 5 | 139 ± 5 | 147 ± 4$^a$ | 148 ± 4$^a$ | 149 ± 3$^a$ | 147 ± 3$^a$ | 142 ± 4$^a$ |
| Ro 20-1724 | 139 ± 6 | 135 ± 7 | 147 ± 8 | 141 ± 6 | 132 ± 7$^b$ | 124 ± 6$^{a,b}$ | 116 ± 7$^{a,b}$ |
| | | | | beats/min | | | |
| HR | | | | | | | |
| Control | 364 ± 15 | 399 ± 13$^a$ | 398 ± 13$^a$ | 393 ± 13$^a$ | 396 ± 15$^a$ | 394 ± 17$^a$ | 390 ± 16$^a$ |
| Ro 20-1724 | 377 ± 20 | 428 ± 12$^a$ | 427 ± 15$^a$ | 431 ± 18$^a$ | 434 ± 24$^a$ | 441 ± 26$^a$ | 449 ± 21$^{a,b}$ |
| Urine Volume | | | | | | | |
| Control | 412 ± 83 | 602 ± 106 | 801 ± 153$^a$ | 947 ± 216$^a$ | 992 ± 215$^a$ | 969 ± 210$^a$ | 865 ± 203$^a$ |
| Ro 20-1724 | 558 ± 123 | 480 ± 176 | 724 ± 261 | 1042 ± 211 | 1329 ± 246$^a$ | 1434 ± 303$^a$ | 1289 ± 302$^a$ |

Values are mean ± S.E.
$^a$P < .05 vs. pre-endotoxin base line.
$^b$P < .05 vs. control.

As seen in Table 2, in both the vehicle-treated and in Ro 20-1724-treated rats that received endotoxin, urine volume gradually increased over the duration of the study. This same pattern was also seen with the time control animals that did not receive endotoxin as discussed above. However, in these endotoxin-treated rats, the urine volume was not significantly different in Ro 20-1724-treated rats than in vehicle-treated rats.

Table 2 also shows that the heart rate of the animals increased after administration of endotoxin in both the vehicle-treated (control) and Ro 20-1724-treated groups. The heart rates of the two groups were statistically significantly different only during the last experimental period (449±21 vs. 390±16 beats/minute in the Ro 20-1724 and vehicle groups, respectively; P=0.0445).

In the vehicle-treated group, mean arterial blood pressure (MABP) was significantly increased during periods 3–7, whereas in the Ro 20-1724-treated group, mean arterial blood pressure was significantly reduced during periods 6 and 7. During periods 5, 6, and 7 mean arterial blood pressure was significantly lower in the Ro 20-1724 group as compared with the corresponding periods in the vehicle group.

In the following example rats were post-treated with the Type IV PDE inhibitor Ro 20-1724 after infusion of endotoxin and before infusion of norepinephrine. The purpose was to determine whether treatment with Ro 20-1724 after endotoxin infusion confers protection against (a) endotoxin-induced acute renal failure, and (b) norepinephrine.

EXAMPLE 2

Methods

Male Sprague-Dawley rats weighing 370–440 g (392±4g; mean ±S.E.; n=48), were obtained from Sasco, Inc. (Omaha, Neb.). The animals were housed for at least 1 week in an animal care facility, with a 12 hour light/dark cycle (7am to 7pm), ambient temperature of 22° C. and a relative humidity of 55%. Institutional guidelines for animal welfare were followed. The rats were fed Wayne Rodent Blox 8604 containing 135 mEq/kg sodium and 254 mEq/kg potassium, and were given water ad libitum. The rats were then anesthetized with Inactin (thiobutabarbital sodium, 100 mg/kg intraperitoneally) and placed on a Deltaphase Isothermal Pad. Body temperature was monitored with a rectal temperature probe thermometer (Physiotemp Instrument, Clifton, N.J.) and maintained at 37±0.5° C. by adjusting a heat lamp positioned above the rats.

Two PE-50 catheters and one PE-10 catheter were inserted into the left jugular vein of each rat. One PE-50 cannula infused saline 0.9% at 80 µl/min and the other PE-50 cannula infused saline 0.9% and later norepinephrine (1 µg/kg/min) at 20 µl/min. The PE-10 tubing infused DMSO or Ro 20-1724 in DMSO at a rate of 4 µl/min, using a model BSP 99 Braintree infusion pump. The left carotid artery was cannulated with a PE-50 catheter, and connected to a digital blood pressure analyzer (Micro-Med, Inc. Louisville, Ky.) for the continuous measurement of mean arterial blood pressure and heart rate. The abdominal cavity was exposed through a midline incision, and the superior mesenteric artery and left renal artery were carefully freed from surrounding tissue. Transit-time blood flow probes (Transonic Systems Inc, Ithaca, N.Y.), model 1RB for the renal artery and model 2SB for the mesenteric artery, were placed around the respective artery and connected to a two-channel, small animal, digital, transit-time blood flowmeter (model T206, Transonics Systems Inc.), and renal blood flow (RBF) and mesenteric blood flow (MBF) were continuously displayed. The left ureter was then cannulated with PE-10 tubing for collection of urine.

After completion of surgery, the 80 µl/min jugular infusion of 0.9% saline was replaced with [$^{14}$C] carboxyl-inulin in 0.9% saline (0.5 µCi followed by 0.035 µCi/min at 80 µl/min). After a 1 hour stabilization period, a 20-min urine clearance period (period 1/CP1), was conducted. All rats then received 20 mg/kg of endotoxin (*Escherichia coli* LPS, Serotype 026:B6; Sigma Chemical Co.) intravenously over 10 minutes, followed by a 30 minute rest period. Two 20-minute clearance periods were then conducted (periods 2–3). The rats then either continued with the DMSO vehicle infusion at 4 µl/min or were given an infusion of Ro 20-1724 (10 µg/kg/min at 4 µl/min) which was continued for the duration of the study (periods 4–8). In some rats, norepinephrine (1 μg/kg/min, at 20 μl/min) was begun at the end of the fourth period, and four more 20 minute clearance periods (5–8) followed, for a total of eight 20 minute clearance periods. At the midpoint of each clearance period, a 150 μl blood sample was collected via the carotid artery for measurement of glomerular filtration rate ("GFR") and hematocrit. Also, during each clearance period, mean arterial blood pressure ("MABP") and heart rate ("HR") were time averaged (1100 Hz), and RBF and MBF were taken as the average of four measurements. Renal vascular resistance ("RVR") and mesenteric vascular resistance ("MVR") were calculated as MABP/RBF and MABF/MBF, respectively. GFR was determined as the renal clearance of [$^{14}$C] carboxyl-inulin, which was quantified with liquid scintillation (Tri-Carb, model 2500 TR, Packard Instrument Co.) analysis of serum and urine samples.

Statistical significance for drug effects on hemodynamic and renal parameters were evaluated using repeated measure analysis of variance (RM-ANOVA) for all survivors (two-factor and three-factor) during periods 5–8 and was performed using the Number Cruncher Statistical System. Statistical significance for drug effects on survival was evaluated using chi-square survival analysis of all the survivors and nonsurvivors and was performed using the Number Cruncher Statistical System. Statistical significance was considered at $p<0.05$.

Results

Of the rats studied in the groups which did not receive norepinephrine, 17 survived the entire protocol (11 of 12 in the Ro 20-1724 group, and 6 of 12 in the vehicle group). In the groups which did receive norepinephrine, 12 survived the entire protocol (8 of 11 in the Ro 20-1724 group, and 4 of 13 in the vehicle group). Table 3 below lists all measured parameters in the four groups before initiation of Ro 20-1724 (or vehicle) and subsequent norephinephrine (or vehicle) infusion. There were no significant differences in any measured parameter between the control and experimental groups at period 3.

TABLE 3

Parameters in Groups During Periods 1, 2, and 3,
Before Initiation of Ro 20-1724 or Vehicle and
Subsequent Norepinephrine or Vehicle Infusion

|  | No NE | | | NE | | |
|---|---|---|---|---|---|---|
|  | Period 1 | Period 2 | Period 3 | Period 1 | Period 2 | Period 3 |
| UcAMP |  |  |  |  |  |  |
| (nmol/20 min) | 2.1 ± 0.2 | 2.4 ± 0.2 | 2.8 0.2 | 2.2 ± 0.2 | 2.6 ± 0.2 | 3.0 ± 0.3 |
| Control | 2.5 ± 0.2 | 2.3 ± 0.2 | 2.5 ± 0.2 | 2.8 ± 0.2 | 2.6 ± 0.2 | 3.3 ± 0.3 |
| Ro 20 |  |  |  |  |  |  |
| RVR |  |  |  |  |  |  |
| (mmHg/[ml/min]) | 12 ± 1.1 | 14 ± 1.5 | 15 ± 1.3 | 10 ± 0.8 | 11 ± 1.0 | 14 ± 2.1 |
| Control | 11 ± 0.6 | 13 ± 0.4 | 13 ± 1.3 | 9.0 ± 0.9 | 10 ± 1.0 | 13 ± 1.4 |
| Ro 20 |  |  |  |  |  |  |
| RBF |  |  |  |  |  |  |
| (ml/min) | 11 ± 1.0 | 10 ± 0.9 | 10 ± 0.8 | 13 ± 1.0 | 13 ± 1.0 | 11 ± 1.0 |
| Control | 12 ± 0.7 | 11 ± 0.7 | 11 ± 0.8 | 15 ± 1.0 | 14 ± 1.0 | 13 ± 1.0 |
| Ro 20 |  |  |  |  |  |  |
| GFR |  |  |  |  |  |  |
| (ml/min) | 1.3 ± 0.1 | 1.2 ± 0.1 | 1.1 ± 0.1 | 1.4 ± 0.1 | 1.1 ± 0.1 | 1.0 ± 0.1 |
| Control | 1.5 ± 0.1 | 1.1 ± 0.1 | 1.1 ± 0.1 | 1.7 ± 0.1 | 1.3 ± 0.1 | 1.2 ± 0.2 |
| Ro 20 |  |  |  |  |  |  |
| MVR |  |  |  |  |  |  |
| (mmHg/[ml/min]) | ND | ND | ND | 13 ± 1.3 | 18 ± 1.6 | 21 ± 2.5 |
| Control | ND | ND | ND | 13 ± 1.4 | 18 ± 2.4 | 20 ± 2.3 |
| Ro 20 |  |  |  |  |  |  |
| MBF |  |  |  |  |  |  |
| (ml/min) | ND | ND | ND | 11 ± 0.9 | 8 ± 0.7 | 7 ± 0.9 |
| Control | ND | ND | ND | 11 ± 1.1 | 9 ± 1.1 | 8 ± 0.8 |
| Ro 20 |  |  |  |  |  |  |
| MABP |  |  |  |  |  |  |
| (mmHg) | 124 ± 3 | 131 ± 4 | 135 ± 4 | 122 ± 3 | 126 ± 5 | 133 ± 5 |
| Control | 129 ± 4 | 132 ± 4 | 137 ± 4 | 129 ± 5 | 135 ± 4 | 142 ± 5 |
| Ro 20 |  |  |  |  |  |  |
| HR |  |  |  |  |  |  |
| (beats/min) | 354 ± 10 | 368 ± 8 | 378 ± 7 | 340 ± 10 | 365 ± 11 | 390 ± 9 |
| Control | 351 ± 7 | 358 ± 8 | 366 ± 8 | 345 ± 9 | 371 ± 11 | 388 ± 9 |
| Ro 20 |  |  |  |  |  |  |

Values are mean ± S.E.
NE = Norepinephrine.
ND = Not determined.

Figure 4A:
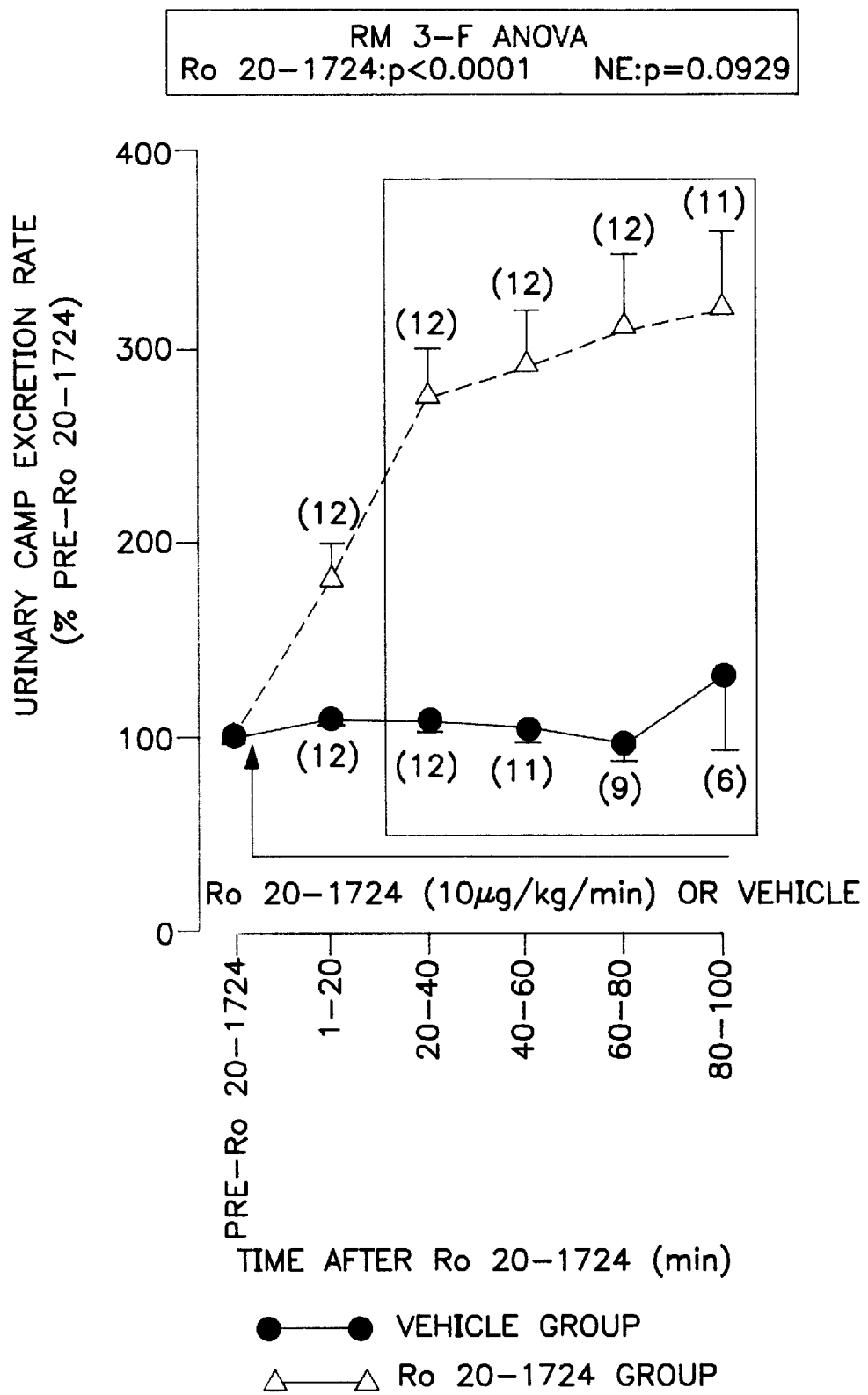
FIGS. 4A and 4B show the effects of post-treatment with Ro 20-1724 70 minutes after endotoxin infusion on urinary cAMP excretion rate in the absence (FIG. 4A) or presence (FIG. 4B) of norepinephrine infusion in endotoxemic rats. Values shown are percent change from pre-Ro 20-1724 baseline represented as mean ±S.E. for all rats (n) at each period. Repeated Measures 3-Factor Analysis Of Variance ("RM 3-F ANOVA") was performed for the last four periods in rats that survived the entire protocol.
Figure 4B:
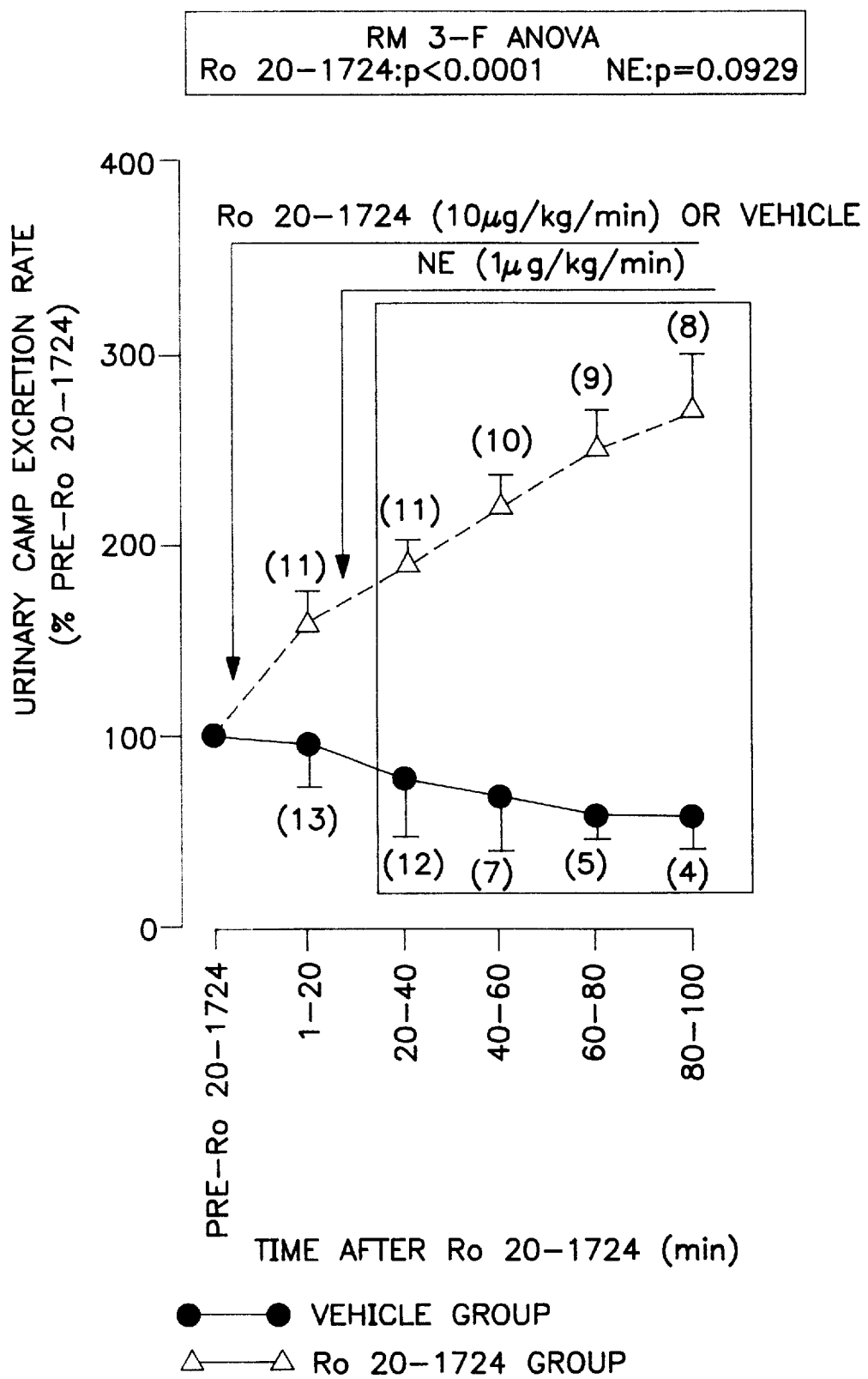
Figure 5A:
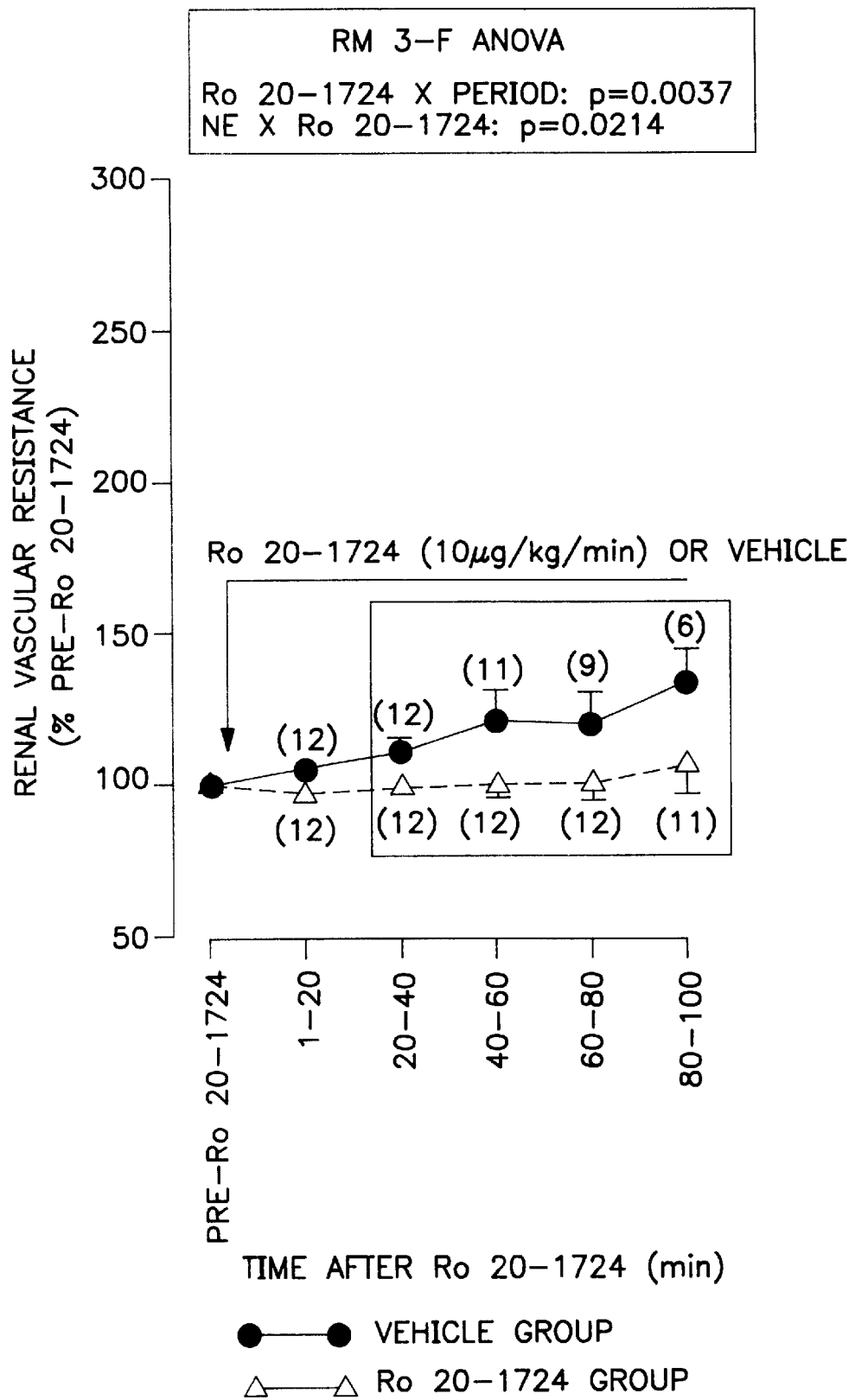
FIGS. 5A and 5B show the effects of post-treatment with Ro 20-1724 70 minutes after endotoxin infusion on renal vascular resistance in the absence (FIG. 5A) and presence (FIG. 5B) of norepinephrine infusion in endotoxemic rats. Values are percent change from pre-Ro 20-1724 baseline represented as mean ±S.E. for all rats (n) at each period. RM 3-F ANOVA was performed for the last four periods in rats that survived the entire protocol.
Figure 5B:
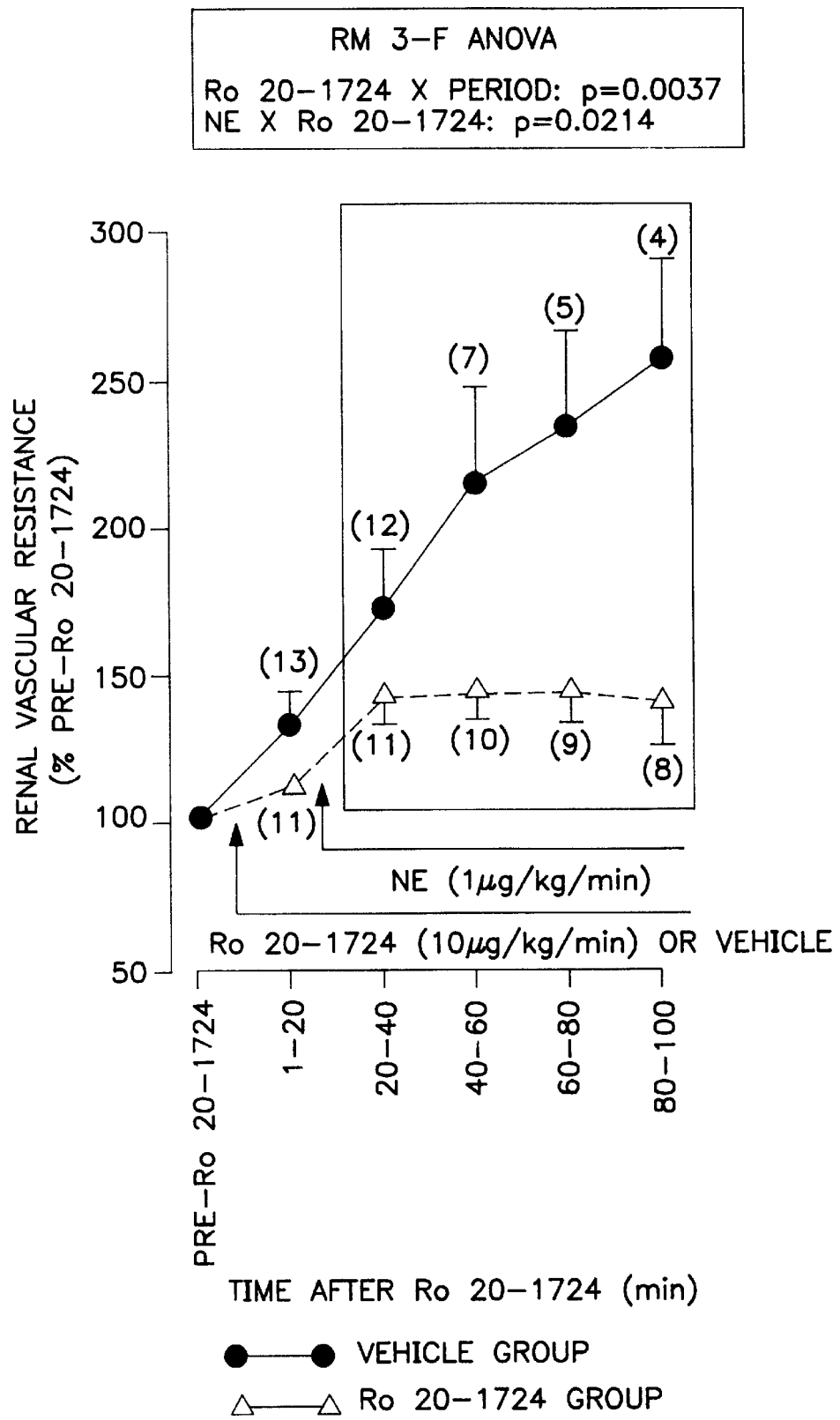
Figure 6A:
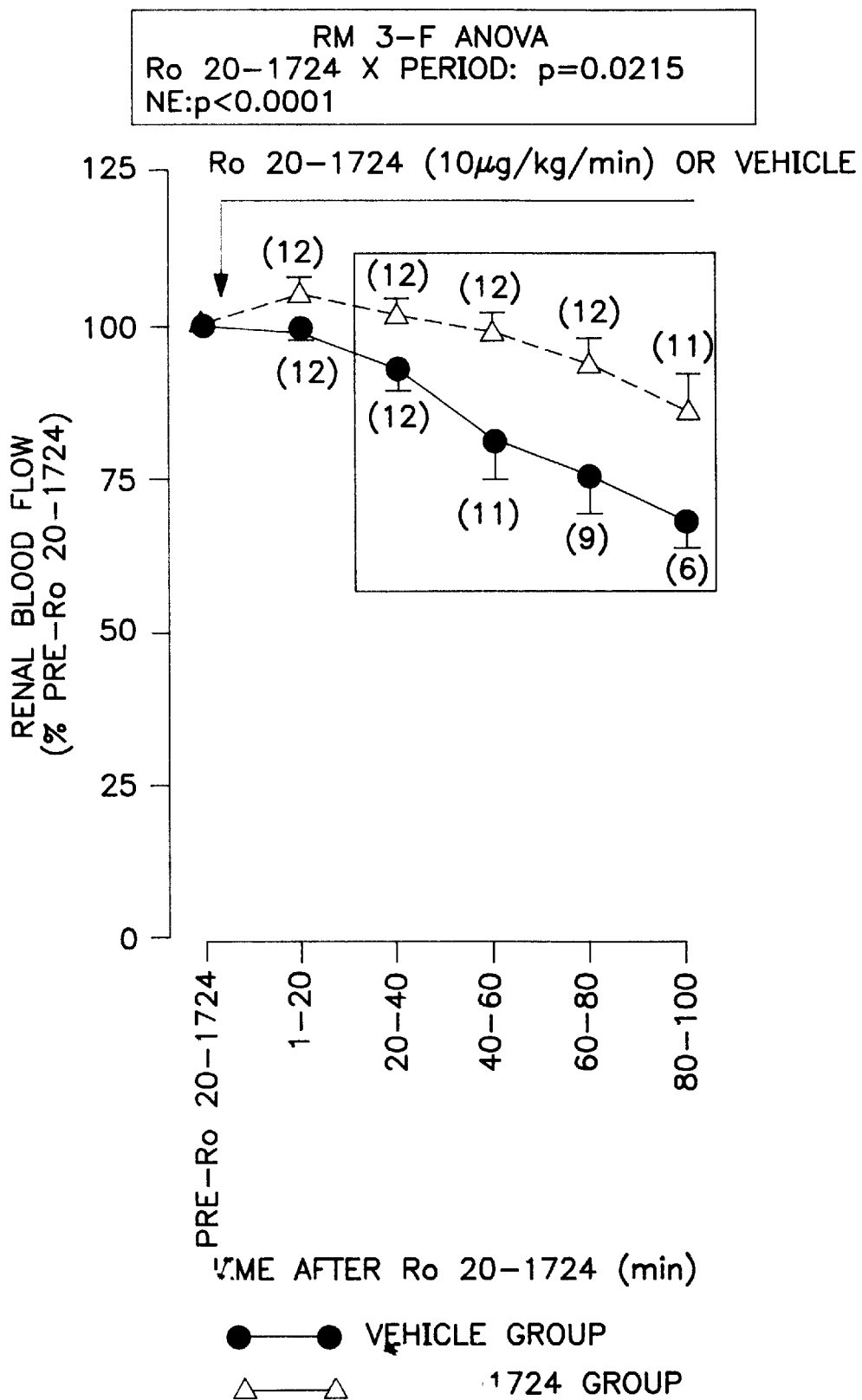
FIGS. 6A and 6B show the effects of post-treatment with Ro 20-1724 70 minutes after endotoxin infusion on renal blood flow in the absence (FIG. 6A) and presence (FIG. 6B) of norepinephrine infusion in endotoxemic rats. Values are percent change from pre-Ro 20-1724 baseline represented as mean ±S.E. for all rats (n) at each period. RM 3-F ANOVA was performed for the last four periods in rats that survived the entire protocol.
Figure 6B:
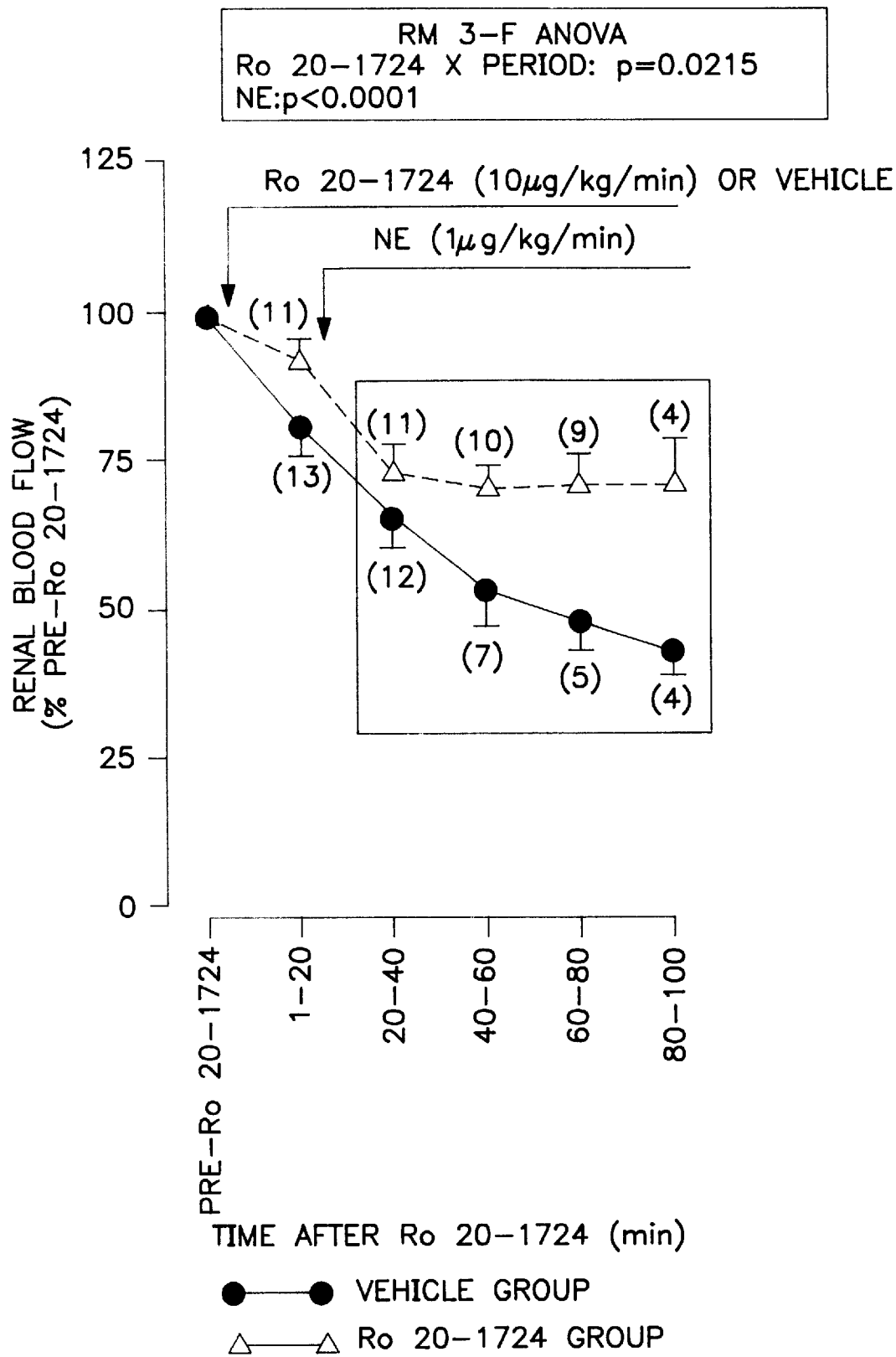
Figure 7A:
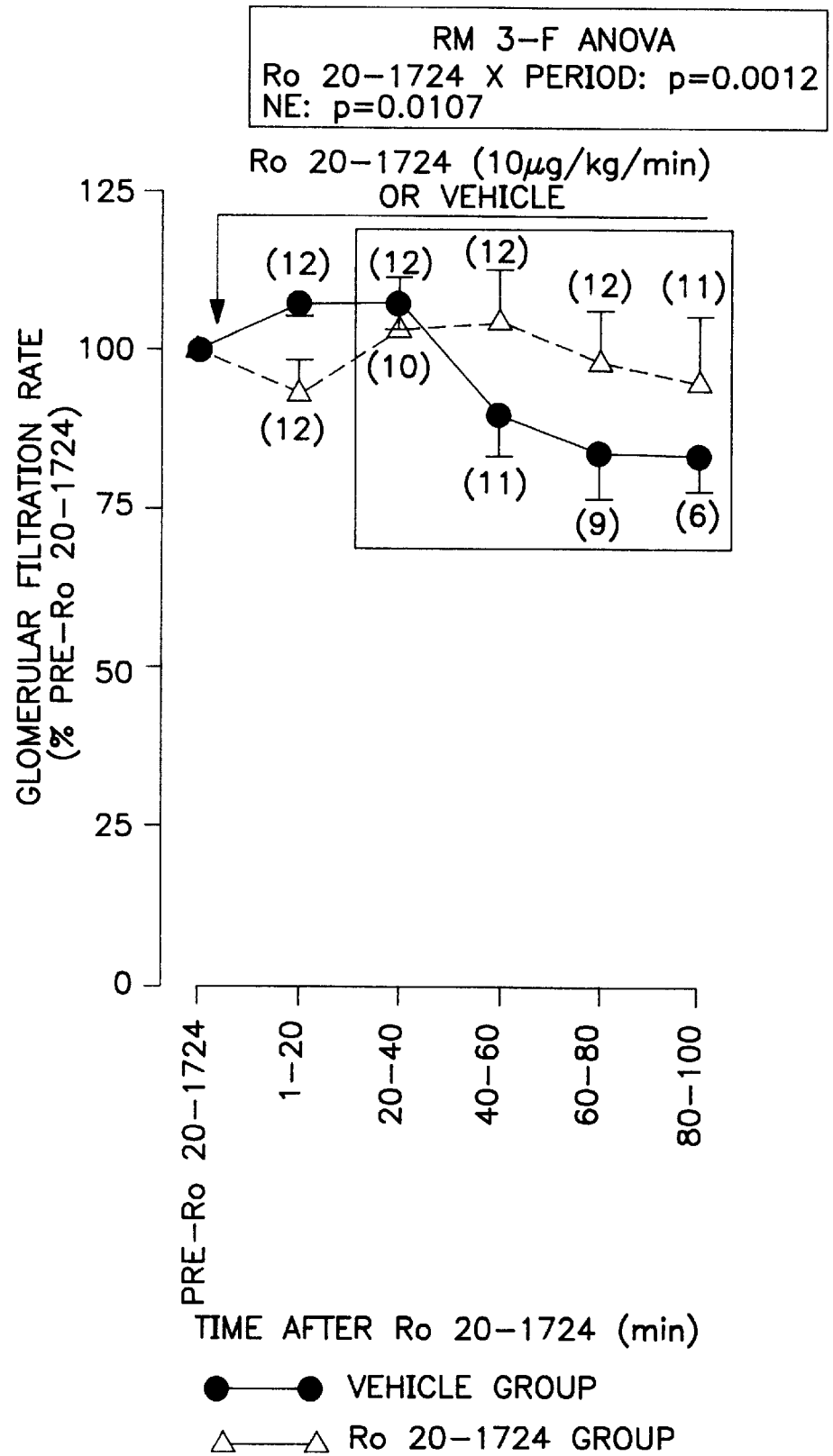
FIGS. 7A and 7B show the effects of post-treatment with Ro 20-1724 70 minutes after endotoxin infusion on glomerular filtration rate in the absence (FIG. 7A) and presence (FIG. 7B) of norepinephrine infusion in endotoxemic rats. Values are percent change from pre-Ro 20-1724 baseline represented as mean ±S.E. for all rats (n) at each period. RM 3-F ANOVA was performed for the last four periods in rats that survived the entire protocol.
Figure 7B:
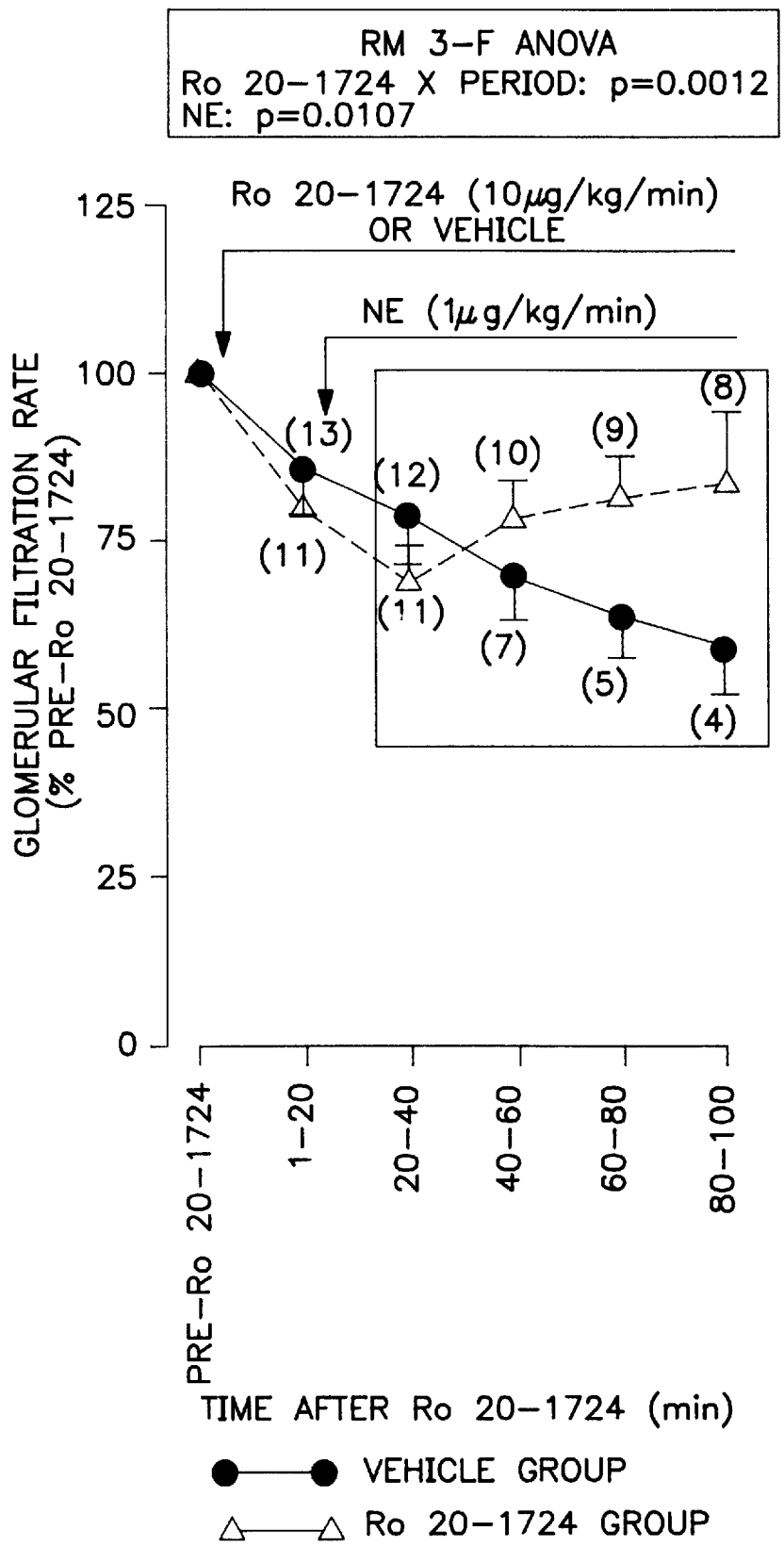
Figure 8A:
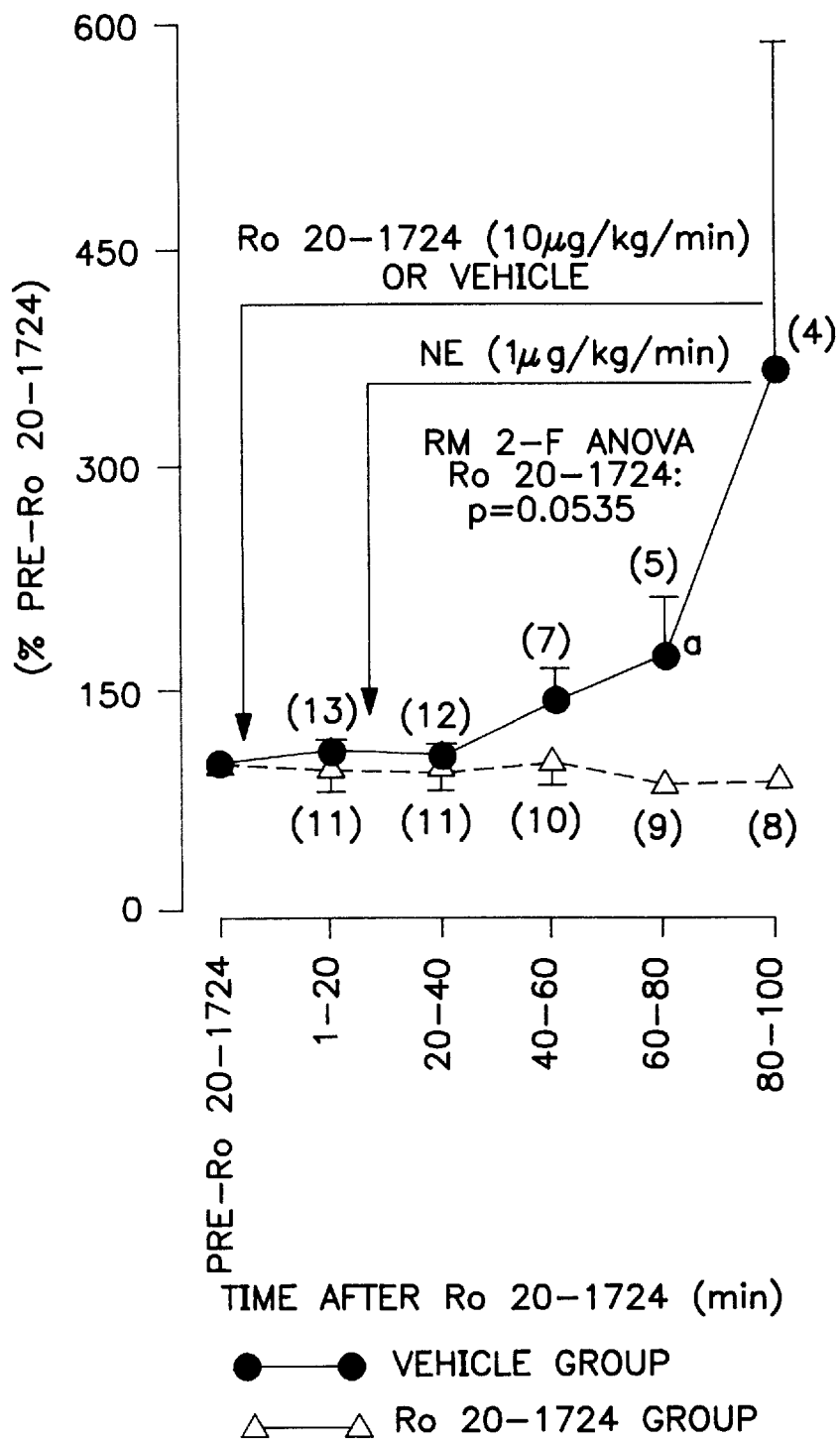
FIGS. 8A and 8B show the effects of post-treatment with Ro 20-1724 70 minutes after endotoxin infusion on mesenteric vascular resistance and mesenteric blood flow, respectively, in the presence of norepinephrine infusion in endotoxemic rats. Values are per cent change from pre-Ro 20-1724 baseline represented as mean ±S.E. for all rats (n) at each period. RM 3-F ANOVA was performed for the last four periods in rats who survived the entire protocol.
Figure 8B:
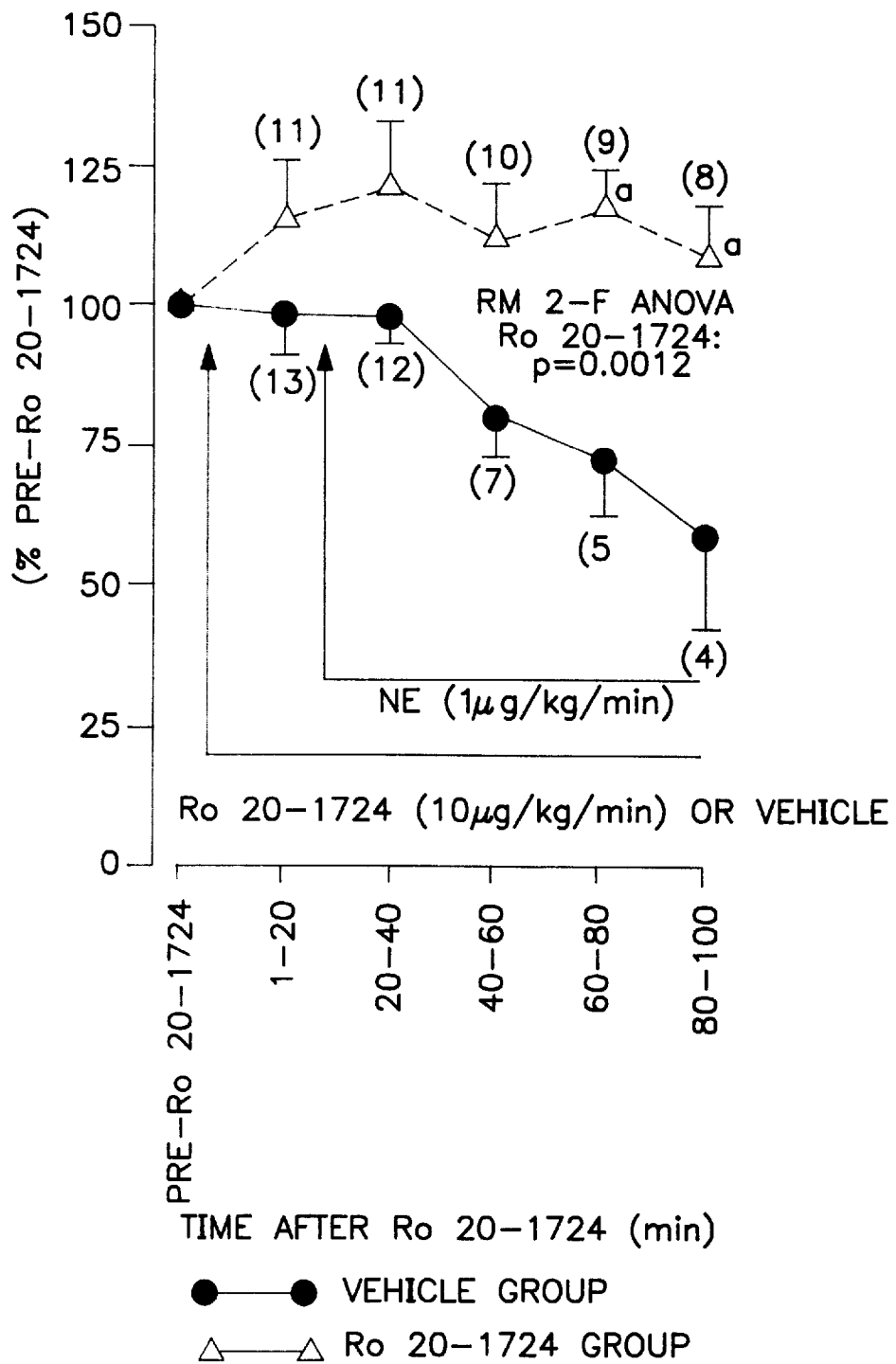

As illustrated in FIGS. 4A and 4B, Ro 20-1724 increased the urinary cAMP excretion of rats that were pre-treated with endotoxin before infusion of Ro 20-1724 by 2- to 3-fold in periods 5 through 8 in the absence and presence of norepinephrine infusion (p<0.0001). The boxes denote the periods that were subjected to statistical analysis. As shown in FIGS. 4A and 4B, Ro 20-1724 elevates cyclic AMP during the last four treatment periods. Accordingly, the statistical anlysis was conducted only on the last four periods which are enclosed in the boxes in FIGS. 4A, 4B, 5A, 5B, 6A, 6B, 7A, 7B and 9A, 9B, 10A, 10B. The results in FIGS. 5A and 5B show that Ro 20-1724 conferred significant protection against endotoxin- and norepinephrine-induced increases in renal vascular resistance (RM 3-F ANOVA; Ro 20-1724×Period: p=0.0037; NE×Ro 20-1724: p=0.0214). In FIGS. 6A and 6B it is seen that Ro 20-1724 significantly protected against endotoxin-induced decreases in renal blood flow in the absence and presence of norepinephrine (RM 3-F ANOVA; Ro 20-1724× Period: p=0.0215). As shown in FIGS. 7A and 7B Ro 20-1724 also conferred significant protection against endotoxin-induced decreases in glomerular filtration rate in the absence and presence of norepinephrine infusion (RM 3-F ANOVA; Ro 20-1724×Period: p=0.0012). Ro 20-1724 completely prevented norepinephrine-induced increases in mesenteric vascular resistance (FIG. 8A) and decreases in mesenteric blood flow during endotoxemia (FIG. 8B) (RM 2-F ANOVA; Ro 20-1724: p=0.0535 for resistance, and p=0.0012 for blood flow).

Figure 9A:
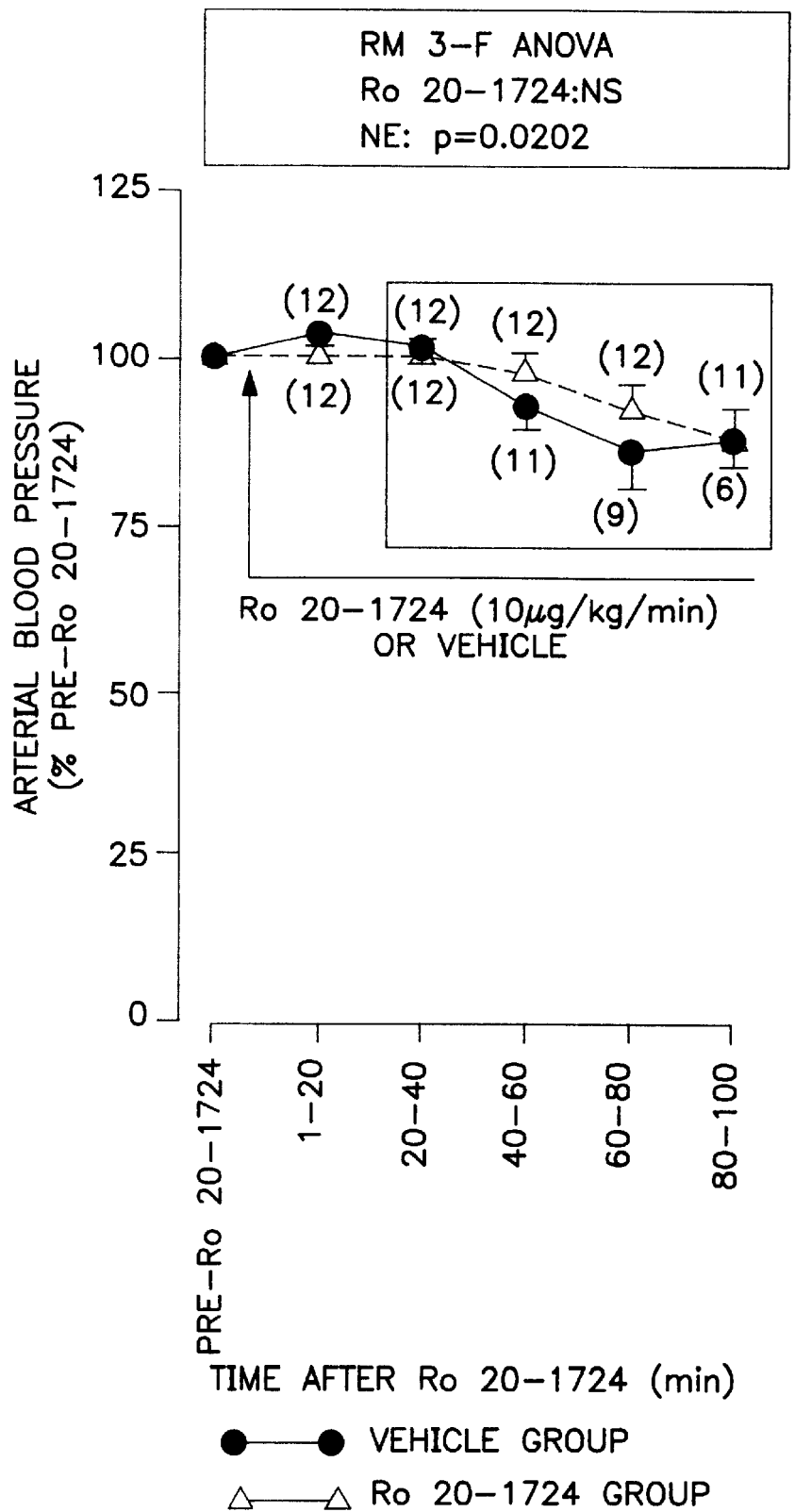
FIGS. 9A and 9B show the effects of post-treatment with Ro 20-1724 70 minutes after endotoxin infusion on mean arterial blood pressure in the absence (FIG. 9A) and presence (FIG. 9B) of norepinephrine infusion in endotoxemic rats. Values are per cent change from pre-Ro 20-1724 baseline represented as mean ±S.E. for all rats (n) at each period. RM 3-F ANOVA was performed in the last four periods in rats who survived the entire protocol.
Figure 9B:
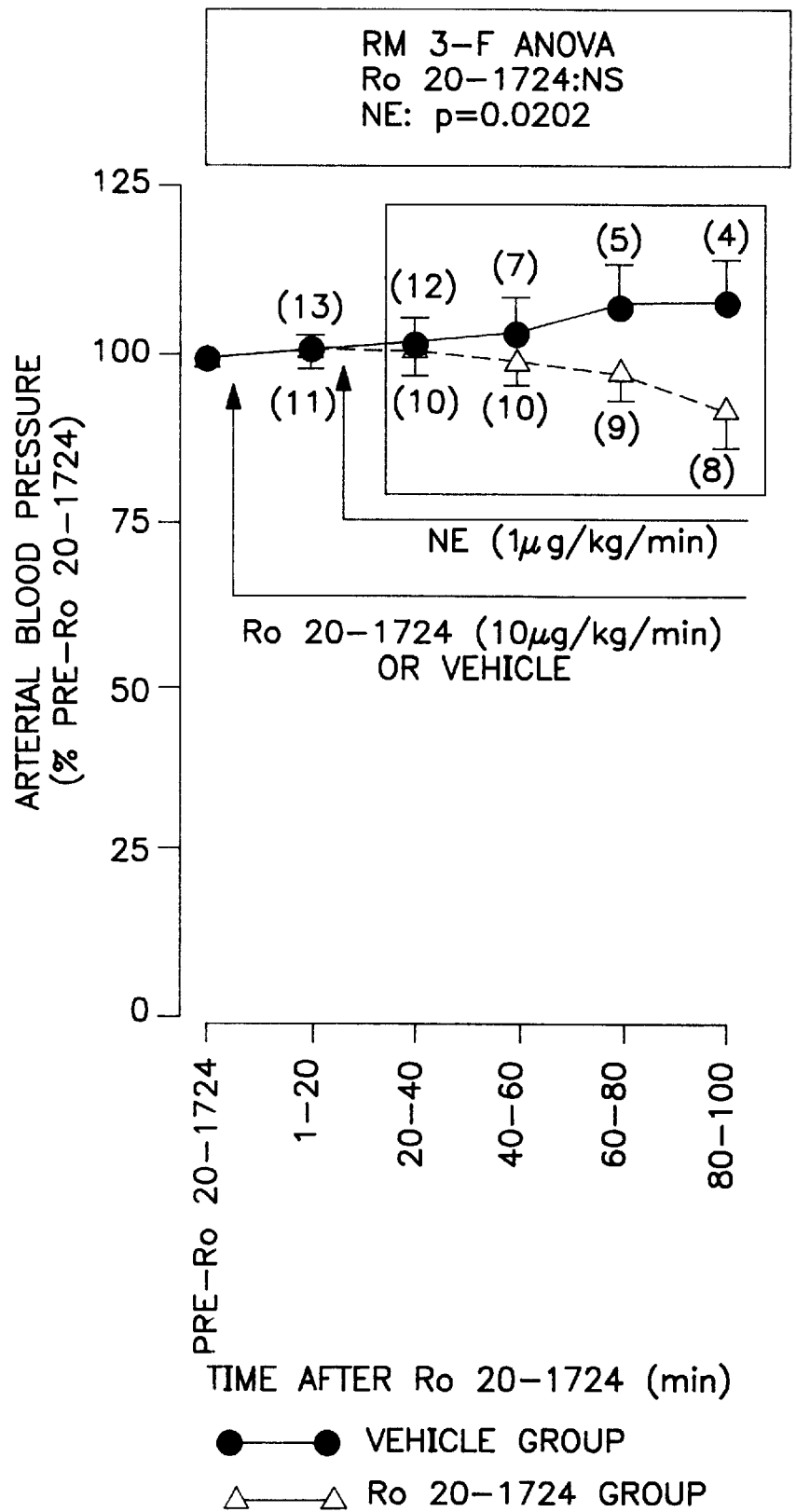
Figure 10A:
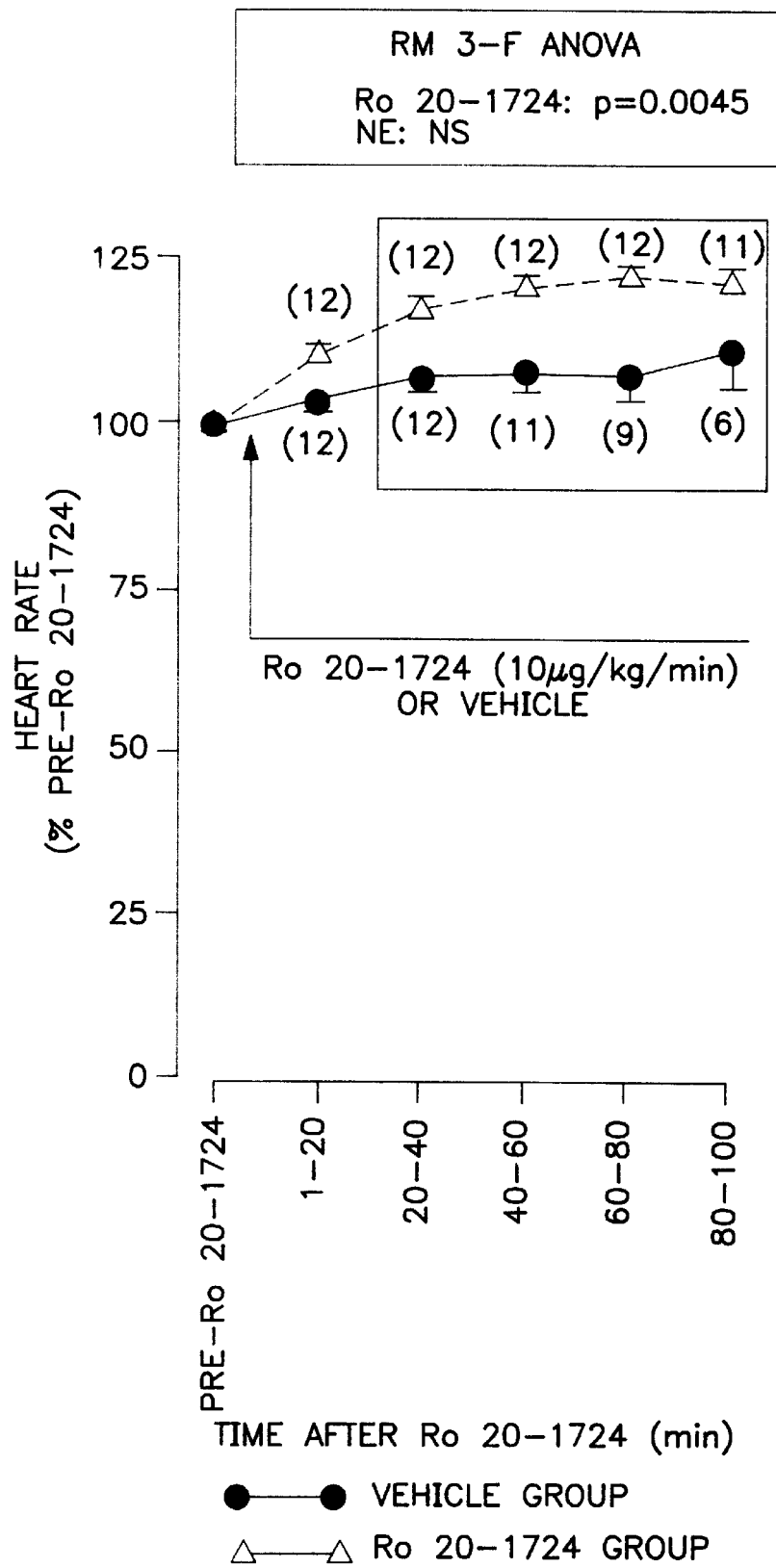
FIGS. 10A and 10B show the effects of post-treatment with Ro 20-1724 70 minutes after endotoxin infusion on heart rate in the absence (FIG. 10A) and presence (FIG. 10B) of norepinephrine infusion in endotoxemic rats. Values are per cent change from pre-Ro 20-1724 baseline represented as mean ±S.E. for all rats (n) at each period. RM 3-F ANOVA was performed for the last four periods in rats who survived the entire protocol.
Figure 10B:
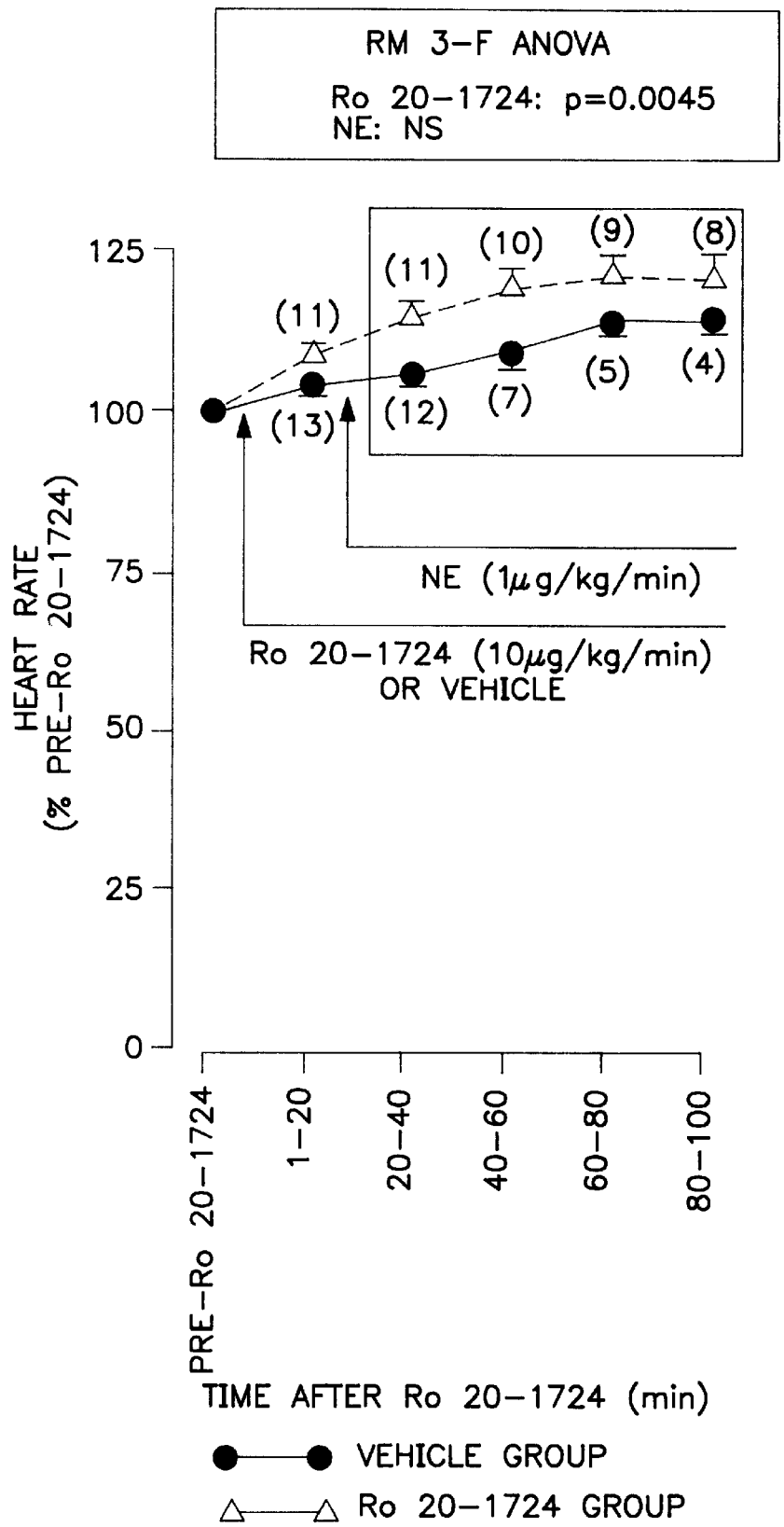

FIGS. 9A and 9B show that Ro 20-1724 had no significant effect on mean arterial blood pressure during endotoxemia in the absence or presence of norepinephrine (RM 3-F ANOVA; Ro 20-1724: NS). However, Ro 20-1724 increased heart rate both in the absence and presence of norepinephrine infusion during endotoxemia (FIGS. 10A and 10B) (RM 3-F ANOVA; Ro 20-1724: p=0.0045).

Figure 11A:
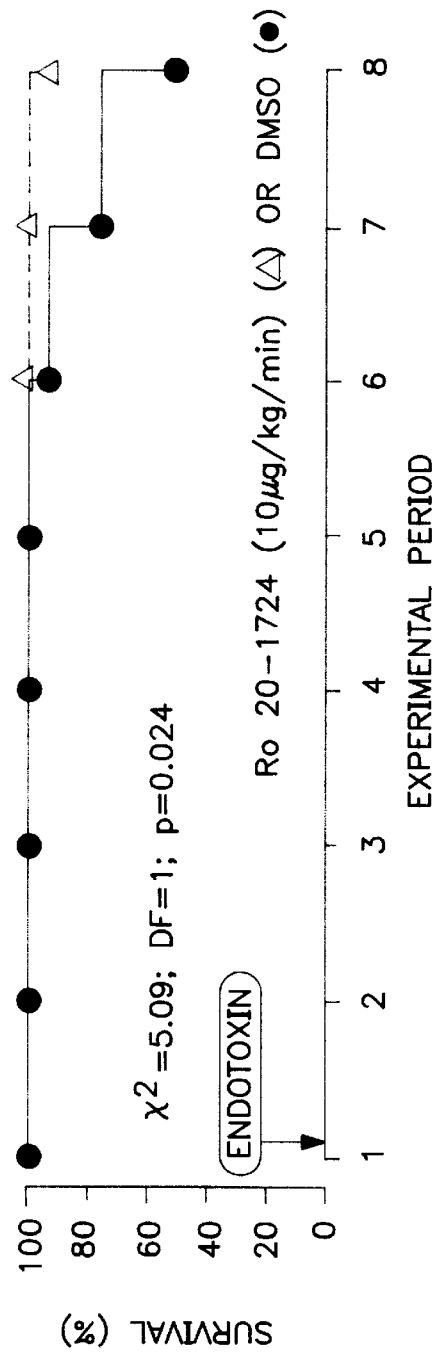
FIGS. 11A and 11B show the effects of post-treatment with Ro 20-1724 after endotoxin infusion on survival in the absence (FIG. 11A) and presence (FIG. 11B) of norepinephrine infusion in endotoxemic rats. Values are per cent survival at each period. Chi-square survival analysis was considered significant if p<0.05.
Figure 11B:
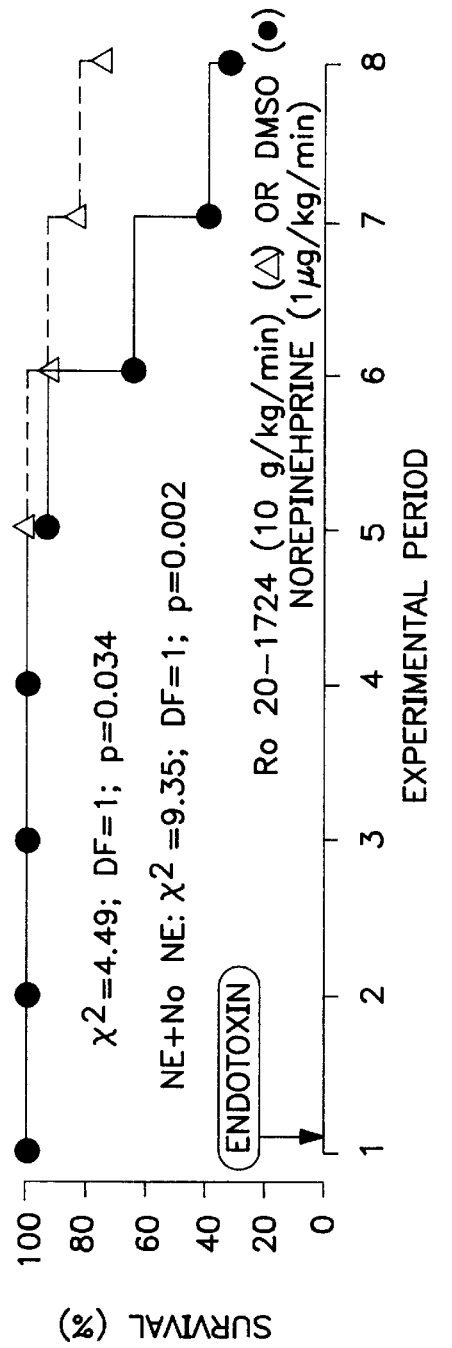

With respect to the ultimate survival of rats, FIGS. 11A and 11B show that Ro 20-1724 improved survival in the absence and presence of norepinephrine infusion during endotoxemia (chi-square; No NE: p=0.024; NE: p=0.034; NE+No NE: p=0.002).

The foregoing shows there are potential therapeutic uses for type IV PDE inhibitors. First, Ro 20-1724 can attenuate endotoxin-induced acute renal failure not only when used as a prophylaxis before endotoxemia is induced but also when used as a treatment after endotoxemia has been established. Second, the above studies show that Ro 20-1724 can prevent norepinephrine-induced renal and mesenteric ischemia without decreasing systemic blood pressure. Third, Ro 20-1724 treatment after the induction of overwhelming endotoxemia in rats can prevent mortality in the presence or absence of vasopressor infusions.

In Example 1 pretreatment with Ro 20-1724 resulted in a 2-to 3-fold increase in urine cAMP levels throughout the study. In Example 2, a post-endotoxin treatment protocol, these levels of increased cAMP excretion did not occur until periods five through eight. Since urine cAMP is a surrogate marker of the pharmacodynamic effect of the PDE inhibitor, the effects of Ro 20-1724 on hemodynamic variables during the periods when urine cAMP levels were increased 2- to 3-fold were therefore studied. It is interesting to note that norepinephrine tended to decrease cAMP excretion rates, an effect that might be explained by the fact that norepinephrine binds to the $\alpha_2$-adrenoceptor which is coupled to inhibition of adenylyl cyclase.

During endotoxemia, the foregoing methods show that renal vascular resistance increased and treatment with Ro 20-1724 prevented this increase. It is also seen that norepinephrine infusion further increased renal vascular resistance, and that Ro 20-1724 also prevented this further increase. Converse changes were noted in renal blood flow, i.e., endotoxemia and norepinephrine decreased renal blood flow, and treatment with Ro 20-1724 attenuated these decreases. Similar findings were seen with glomerular filtration rate. Endotoxemia decreased glomerular filtration rate, and treatment with Ro 20-1724 prevented this decrease. Norepinephrine further decreased glomerular filtration rate, and Ro 20-1724 also protected against this effect. Taken together, these data indicate that Ro 20-1724 protects against endotoxin-induced and norepinephrine-induced acute renal failure even when Ro 20-1724 is given after endotoxemia has been established.

Perfusion to the mesenteric vascular bed is extremely important during sepsis and endotoxemia, and can be particularly compromised during norephinephrine infusion. In the model of endotoxemia described herein, norepinephrine decreased mesenteric blood flow and increased mesenteric vascular resistance. Ro 20-1724 actually restored mesenteric blood flow to pre-endotoxin levels in part by preventing any norepinephrine induced increase in mesenteric vascular resistance. This marked effect on mesenteric blood flow is of considerable importance since it is theorized that the development of the multiple organ failure syndrome and death in sepsis is due in part to inadequate perfusion of the intestine and liver. See, Landow L., et al., *Acta. Anaesthes. Scand.* 38(7):626 (1994) and Liu, P., et al., *Shock* 3(1):56 (1995) the disclosures of which are incorporated herein by reference. The observation that Ro 20-1724 is able to increase blood flow in the mesentery but only maintain blood flow in the kidney could be indicative of unique differences in type IV PDE distribution in the mesenteric and renal microcirculation.

The studies of Example 2 show that norepinephrine increased mean arterial blood pressure by less than 10 percent. Ro 20-1724 had no statistically significant effect on systemic blood pressure in the presence or absence of norepinephrine. Since Ro-20-1724 did affect renal and mesenteric vascular resistance this observation suggests that the type IV specific PDE inhibitor may have specific effects in the renal and mesenteric beds without affecting the systemic vasculature.

In order to be certain that Type IV PDE inhibition was not harmful, survival data was also examined. Ro 20-1724 conferred a significant improvement in survival of subjects during endotoxemia both in the presence and in the absence of vasopressor therapy. Others had previously shown improved survival in galactosamine sensitized mouse endotoxemia models (Sekut et al, 1995). This study establishes that it is unlikely that there is any fatal drug interaction between the type IV PDE inhibitors and catecholamine-based vasopressors. This is particularly important because the vast majority of patients with endotoxemia and sepsis require catecholamine infusions to maintain blood pressure and perfusion.

The mechanism by which PDE type IV inhibitors prevent endotoxin and catecholamine-induced renal and mesenteric vasoconstriction and improve survival are not understood. Other investigators have reported that inflammatory cells including monocytes and macrophages have a preponderance of Type IV PDE. Inhibition of this specific PDE with rolipram, CP-77059, and Ro 20-1724 has been reported to result in decreased production of tumor necrosis factor (TNF) (See, for example, Kambayashi, T., et al., *J. Immun.* 155:4909 (1995) and Verghese, M., et al., *J. Pharmacol.*

*Exp. Ther.* 272:1313 (1995), the disclosures of which are incorporated herein by reference). It has recently been shown that PDE IV inhibition increases production of IL-10, the anti-inflammatory cytokine, in endotoxin-stimulated mouse macrophages which in turn inhibits production TNF and IL-6 (Kambayashi, T., et al., *J. Immun.* 155:4909 (1995). Investigators have also shown that Type IV PDE inhibitors decrease TNF-α production and improve survival in galactosamine sensitized mice after endotoxin exposure (Sekut, L., et al., *Clin. Exp. Immunol.* 100(1):126 (1995)). It has also been shown that these inhibitors decrease the eosinophil respiratory burst (Dent, G., et al., *J. Pharmacol. Exp. Ther.* 271:1167 (1994)), inhibit the formation of reactive $O_2$ metabolites in glomeruli (Chini, C. C., et al., *Kidney Int.* 46:218 (1994), and protect against endotoxin induced liver injury in mouse models (Fisher, W., et al., *Biochem. Pharmacol.* 45:2399 (1993)).

Rolipram and Ro 20-1724 are both PDE type IV inhibitors which have been extensively studied in human trials as anti-inflammatory agents for asthma and anti-depressant agents for depression. See, Beavo, J. A., et al., *Mol. Pharmacol.* 46:399 (1994), the disclosure of which is incorporated herein by reference. The drugs are remarkably safe with nausea being the dose limiting side effect. Patients with endotoxemia and sepsis are usually sedated and anesthetized in the intensive care setting. The major potential side effects of type IV PDE inhibitors in critical care medicine would therefore most likely center on possible interactions with concomitantly used drugs to maintain survivability during septic shock. Therapeutic agents which stimulate adenylyl cyclase and increase cAMP production would be expected to have increased potency in selected tissue in the presence of the selective PDE inhibitors. As a first step, we have examined the interaction of the predominant catecholamine vasopressor, norepinephrine, with Ro 20-1724 and found no deleterious interaction.

The foregoing results of the present invention shows that pre-treatment as well as post-treatment with a PDE type IV inhibitor effectively attenuates the development of endotoxin-induced renal failure. It has been shown that PDE type IV inhibition also protects against norepinephrine induced mesenteric and renal ischemia during endotoxemia. Thus there can be a role for the use of PDE type IV inhibitors to protect mesenteric and renal blood flow during vasopressor infusions. The observation of the present invention that PDE type IV inhibition improves survival when used as a treatment for endotoxemia in the presence or absence of vasopressor infusions supports future study of these agents as therapies in human endotoxemia and septic shock.

Although the invention has been described in detail for the purposes of illustration, it is to be understood that such detail is solely for that purpose and that variations can be made therein by those skilled in the art without departing from the spirit and scope of the invention except as it may be limited by the claims.

We claim:

1. A method for protecting a human subject in need thereof from developing acute renal failure resulting from septicemia/endotoxemia, comprising the step of administering to said subject prior to the onset of septicemia/endotoxemia a therapeutically effective amount of a composition comprising at least one drug with Type IV phosphodiesterase inhibiting activity or any combination thereof and a pharmaceutically acceptable carrier.

2. The method of claim 1, wherein said drug with Type IV phosphodiesterase inhibiting activity is 4-[(3-butoxy-4-methoxyphenyl)methyl]-2-imidazolidinone.

3. A method for protecting a human subject in need thereof from developing acute renal failure or treating acute renal failure in a human subject resulting from septicemia/endotoxemia comprising the step of administering to said subject after the onset of septicemia/endotoxemia a therapeutically effective amount of a composition comprising at least one drug with Type IV phosphodiesterase inhibiting activity or any combination thereof and a pharmaceutically acceptable carrier.

4. The method of claim 3, wherein said drug with Type IV phosphodiesterase inhibiting activity is 4-[(3-butoxy-4-methoxyphenyl)methyl]-2-imidazolidinone.

* * * * *